United States Patent
Hands et al.

(10) Patent No.: US 12,216,010 B2
(45) Date of Patent: Feb. 4, 2025

(54) FLEXIBLE DEVICES INCORPORATING ELECTRONICALLY-CONDUCTIVE LAYERS, INCLUDING FLEXIBLE WIRELESS LC SENSORS

(71) Applicants: THE UNIVERSITY COURT OF THE UNIVERSITY OF EDINBURGH, Edinburgh (GB); HERIOT-WATT UNIVERSITY, Edinburgh (GB)

(72) Inventors: Philip James Walton Hands, Edinburgh (GB); Vasileios Mitrakos, Edinburgh (GB); Lisa Miriam MacIntyre, Edinburgh (GB); Marc Philippe Yves Desmulliez, Edinburgh (GB)

(73) Assignees: THE UNIVERSITY COURT OF THE UNIVERSITY OF EDINBURGH, Edinburgh (GB); HERIOT-WATT UNIVERSITY, Edinburgh (GB)

(*) Notice: Subject to any disclaimer, the term of this patent is extended or adjusted under 35 U.S.C. 154(b) by 338 days.

(21) Appl. No.: 17/801,740

(22) PCT Filed: Feb. 26, 2021

(86) PCT No.: PCT/GB2021/050500
§ 371 (c)(1),
(2) Date: Aug. 23, 2022

(87) PCT Pub. No.: WO2021/171037
PCT Pub. Date: Sep. 2, 2021

(65) Prior Publication Data
US 2023/0078471 A1    Mar. 16, 2023

(30) Foreign Application Priority Data
Feb. 28, 2020 (GB) .................. 2002869

(51) Int. Cl.
*G01L 1/14* (2006.01)
*H05K 3/02* (2006.01)
*H05K 3/46* (2006.01)

(52) U.S. Cl.
CPC ............. *G01L 1/146* (2013.01); *G01L 1/144* (2013.01); *H05K 3/02* (2013.01); *H05K 3/4673* (2013.01)

(58) Field of Classification Search
CPC .......... G01L 1/146; G01L 1/144; H05K 3/02; H05K 3/0064; H05K 3/4673
See application file for complete search history.

(56) References Cited

U.S. PATENT DOCUMENTS

2018/0012861 A1* 1/2018 Oh .................... H01L 24/83

FOREIGN PATENT DOCUMENTS

| CN | 108507621 A | 9/2018 |
| CN | 110115581 A | 8/2019 |
| CN | 110631750 A | 12/2019 |

OTHER PUBLICATIONS

Takei, Atsushi, et al. "Stretchable and durable Parylene/PEDOT:PSS/Parylene multi-layer induced by plastic deformation for stretchable device using functionalized PDMS". AIP Advances, Feb. 1, 2020; 10 (2): 025205. (Year: 2020).*

(Continued)

*Primary Examiner* — Paul M. West
(74) *Attorney, Agent, or Firm* — Foley & Lardner LLP

(57) ABSTRACT

There is described a method of producing a flexible structure and sensor devices incorporating the former, such as wireless LC sensors, that comprises a plurality of thin-film layers of elastomeric material and at least one layer of micro-wrinkled electrically conductive material. The method includes steps leading to 2D wrinkled metallised polydimethylsiloxane (PDMS) layers enabling considerable flexibil- (Continued)

ity with negligible bending failure for angles up to 180 degrees.

20 Claims, 14 Drawing Sheets

(56) References Cited

OTHER PUBLICATIONS

International Search Report and Written Opinion on PCT/GB2021/050500 mailed on May 20, 2021 (11 pages).

Ji Bowen et al, "Wrinkled Microelectrode Interface Based on Oil-Pretreated Hyperelastic Substrate", 2019 IEEE 32nd International Conference on Micro Electro Mechanical Systems (MEMS), IEEE, Jan. 27, 2019 (Jan. 27, 2019), p. 561-564.

Sakhdari Maryam et al, "Ultrasensitive telemetric sensor based on adapted parity-time symmetry", 2017 IEEE International Symposium on Antennas and Propagation & USNC/URSI National Radio Science Meeting, IEEE, Jul. 9, 2017 (Jul. 9, 2017), p. 579-580.

* cited by examiner

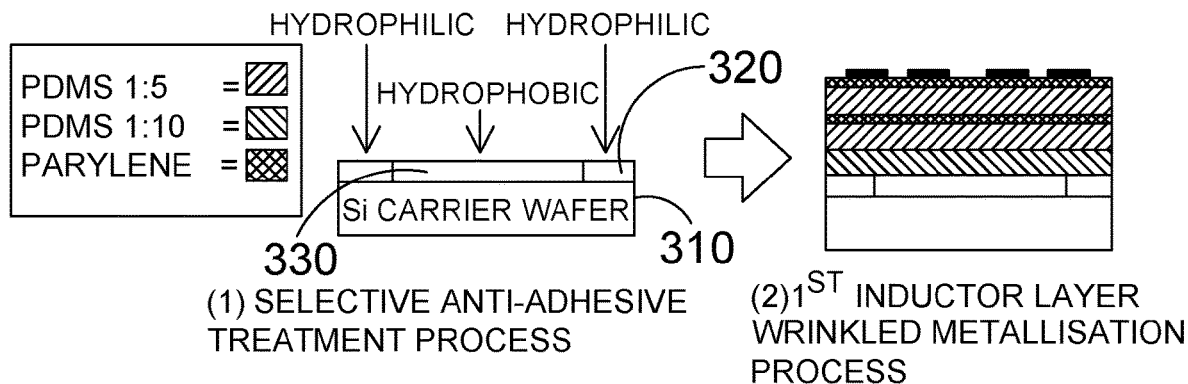
FIG. 3A (1) SELECTIVE ANTI-ADHESIVE TREATMENT PROCESS
FIG. 3B (2) 1ST INDUCTOR LAYER WRINKLED METALLISATION PROCESS
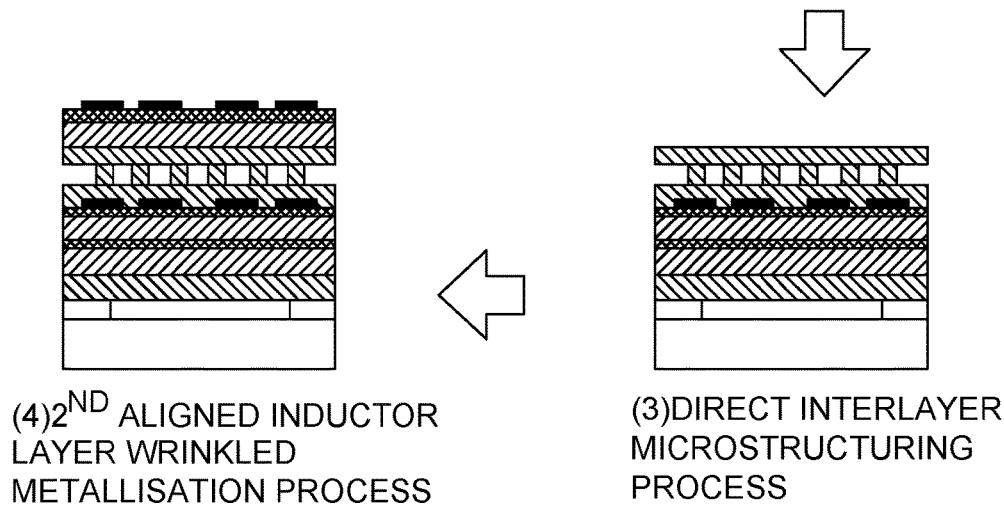
FIG. 3D (4) 2ND ALIGNED INDUCTOR LAYER WRINKLED METALLISATION PROCESS
FIG. 3C (3) DIRECT INTERLAYER MICROSTRUCTURING PROCESS
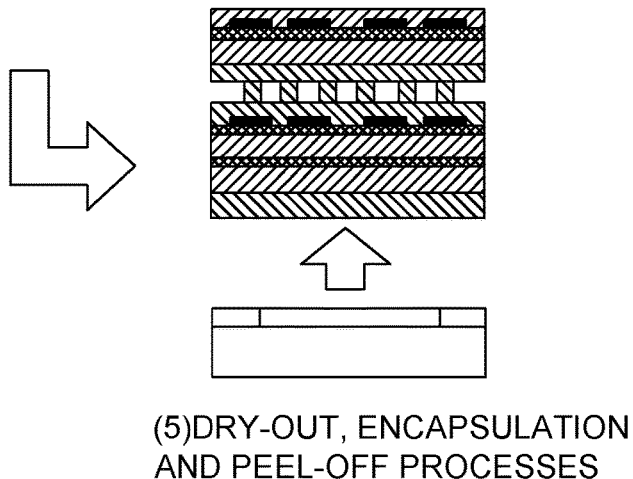
FIG. 3E (5) DRY-OUT, ENCAPSULATION AND PEEL-OFF PROCESSES

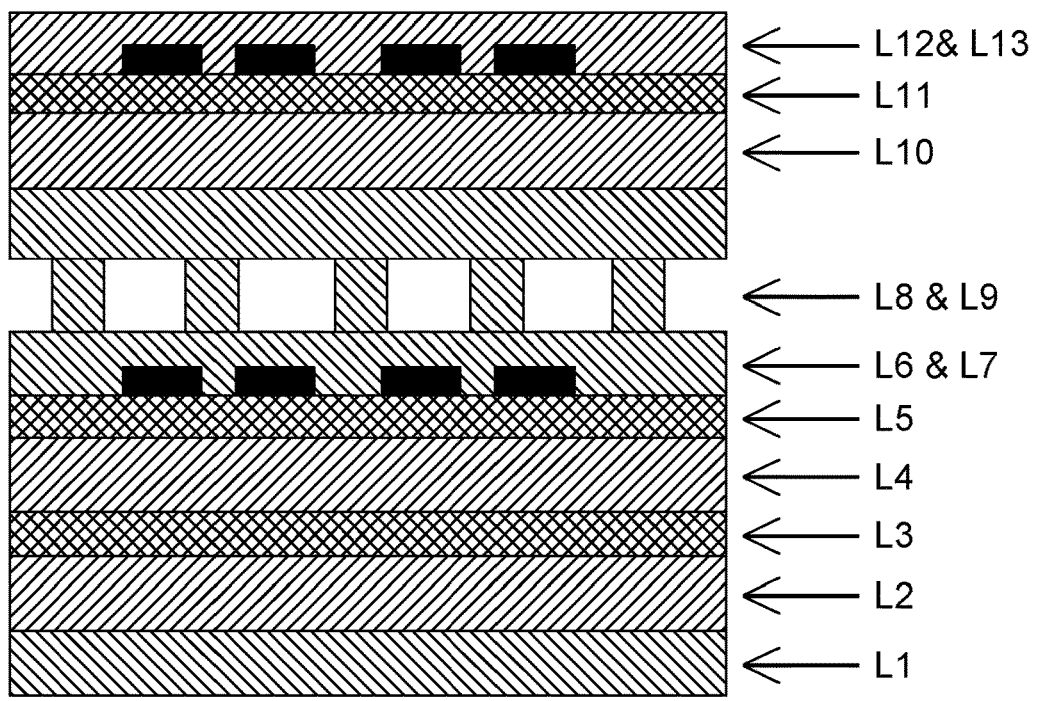
FIG. 4
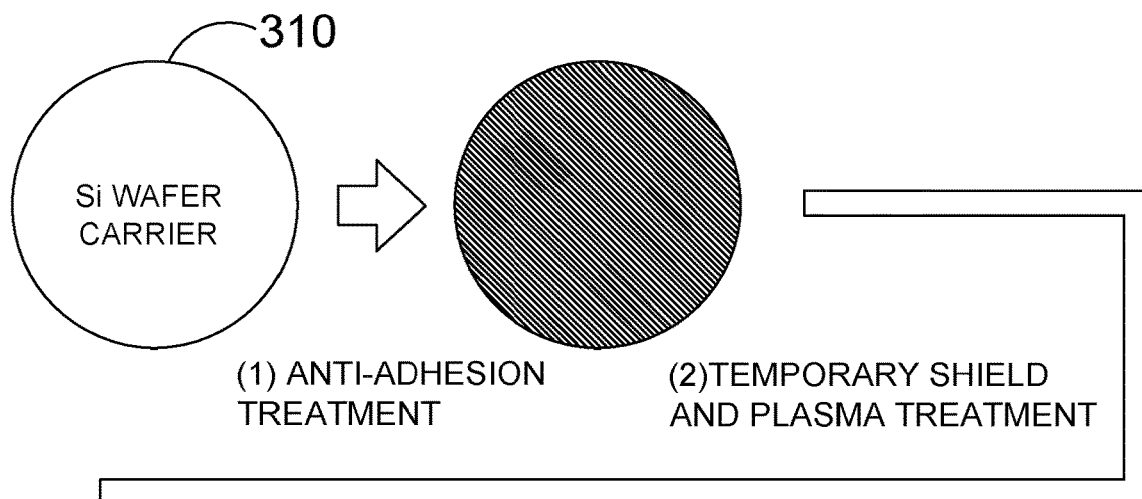
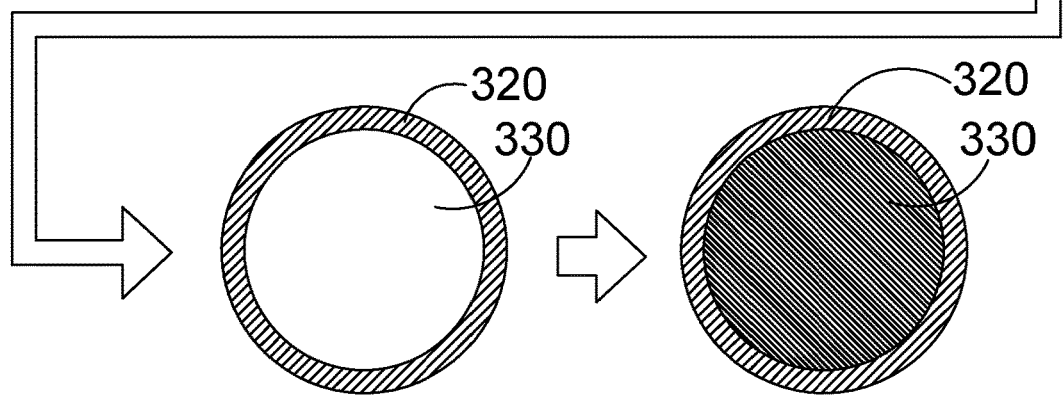
FIG. 5A

FLEXIBLE DEVICES INCORPORATING ELECTRONICALLY-CONDUCTIVE LAYERS, INCLUDING FLEXIBLE WIRELESS LC SENSORS

CROSS-REFERENCE TO RELATED APPLICATIONS

This application is a U.S. National Stage Application under 35 U.S.C. § 371 of International Patent Application No. PCT/GB2021/050500, filed on Feb. 26, 2021, which claims priority to Great Britain Patent Application No. 2002869.2, filed on Feb. 28, 2020, the content of each of which is incorporated herein by reference in their entireties.

FIELD

The invention relates to flexible devices that incorporate flexible electrically-conductive layers and methods of fabricating such devices using thin-film layers of Parylene and PDMS (polydimethylsiloxane, also known as dimethylpolysiloxane or dimethicone). Devices according to the invention include flexible wireless LC thin-film individual sensors or sensor arrays. The methods of manufacturing such devices, include methods of producing microscale wrinkled conductive (usually metallic) layers on PDMS thin-film substrates, development of an embedded PDMS thin-film microstructured layer, and bottom-up wafer-scale sensor assembly.

BACKGROUND

The invention adopts known principles of:
Aligned double-inductor inductive/capacitive (LC) sensors being good resonant tanks for inductive wireless communication without the need for power supply.
PDMS elastomer (characterised by low Young's modulus) being a biocompatible 'gold standard' material for wearable technologies, flexible sensors and bioelectronics and the current limitations in metal deposition on PDMS
Elastomeric microstructured dielectric media exhibiting superior performance to deformation against uniform or air-gap mediums within the field of flexible sensors, such as, increased and tunable low-pressure sensitivity and ultra-fast (~ms) highly repeatable spring response to compressive cycling with no viscoelastic creep
The industry standard semiconductor microfabrication processing approach for mass wafer-based batch production, such as photolithography, bottom-up layer-by-layer structuring, photolithographic self-alignment, and thin-film layer deposition via means of spin-coating, sputtering and evaporation.

Successful mass manufacture of high-yield flexible thin-film LC pressure sensor arrays rests on achieving a high degree of translational and angular precision alignment of the double-inductor structure. This challenge is combined with the difficulty in the integration during processing of the pressure-sensitive microstructured interlayer. Thus far thin-film elastomer-only LC sensor arrays on a large-scale have been difficult to mass produce due to:
(1) the crack formation of microscale metallic structures on thin-film elastomeric substrates, such as PDMS, following deposition, deformation or bending, resulting in the current use of less flexible/conformable substrates for the inductive structures;
(2) the soft lithography fabrication methods used on flexible substrates for the formation of the microstructured layer which do not comply with a bottom-up large-scale sensor assembly approach; and
(3) the reliance on non-scalable methods used in the development of each sensor layer separately and assembly of the sensor structure via means of mechanical alignment, high pressure and lamination under heat, which produce misalignment of the two inductors' tracks and non-uniformity of the structure and thus performance degradation of the sensor arrays on a large scale.

Pressure sensors employing passive LC sensor design are well established as flexible sensors for competing applications (e.g. medical sensors, robotics).

However, most rely on ceramic or polyimide structures which are either not as flexible, biocompatible, or do not comply with the industry-standard semiconductor processing—whereas the present invention is PDMS-only and thus entirely biocompatible and flexible.

Furthermore, soft lithography is usually used for thin-film PDMS, but embodiments of the method of fabrication described herein employ specific sacrificial moulding on thin film that allows, concurrently, bottom-up layering, microstructuring and precise alignment of the inductive thin-film layers of the sensor arrays; and thus produces high-yield, high-performance sensors on flexible material on a wafer-scale. The entirely novel 2D-wrinkled metallised PDMS layers allow for unprecedented levels of flexibility without the metal cracking under deformation.

SUMMARY

Aspects of the invention to enable the above include, primarily, a novel method of assembling, bottom-up, devices such as LC microsensors by aligning thin-film elastomers with 2D-wrinkled electrically-conductive, particularly metallised, surfaces and, secondarily, a variable microstructure intralayer of a micro-frustum array geometry created by a sacrificial mould of a tunable angle, unlike standard soft lithography techniques which primarily rely on pre-etched Silicon moulds and result in set frustum angles.

This method of fabrication thus is able to yield, for example, an inventive wireless flexible LC sensor array, comprising two thin-film PDMS inductor layers with 2D wrinkled surfaces and aligned metal tracks, sandwiching a microstructured thin-film intralayer. Each sensor unit in an array of sensor units formed in a single process on a single wafer may be the same or different from other sensor units in the sensor array; e.g. the parameters of individual sensor units in the array may be varied such that each sensor unit has a unique resonant frequency.

The methods of fabrication disclosed herein lend themselves to mass batch wafer treatment to produce, for example, different sensors simultaneously with high precision alignment and thus high yield at a reduced manufacturing cost. OK Flexible, dense thin-film sensor arrays—as a result of the fabrication method—have high precision alignment and structural uniformity of layers ensuring considerably high performance. The passive electromechanical LC design of certain sensors embodying the invention (which is not novel in itself but has previously been lacking performance in flexible electronics due to misalignment and the use of less flexible materials) allows power-supply-free wireless signal communication.

The 2D wrinkled metallised PDMS layers provided by embodiments of the invention enable considerable flexibility with negligible bending failure for angles up to 180°.

In broad terms, methods according to aspects of the invention comprise processing a carrier substrate (usually a silicon wafer) to ensure strong adhesion to the periphery of the substrate of a first PDMS thin-film layer subsequently applied to the substrate and low adhesion of the PDMS layer to the main central area of the substrate. One or more additional thin-film layers of PDMS of progressively increasing Young's modulus are applied to establish a gradient of reducing elasticity, followed by a thin-film layer of Parylene. The substrate is immersed in a solvent for a period of time sufficient to induce low-intensity swelling in the PDMS layers. A further thin-film layer of PDMS is applied, followed by a further thin-film layer of Parylene. The Parylene layers are applied by vacuum deposition. During vacuum deposition of the further Parylene layer, diffusion of the solvent from the PDMS layers, in combination with the strong adhesion of the periphery of the first PDMS layer to the substrate, the elasticity gradient, the initial Parlyene layer and the subsequent PDMS layer, results in permanent, uniform micro-scale wrinkling of the further Parylene layer. This micro-wrinkling is reflected in a subsequent electrically-conductive (e.g. metallic) layer applied to the wrinkled Parylene, so that the wrinkled electrically-conductive layer is highly flexible (can be bent without cracking). The same wrinkling mechanism can be exploited in further subsequently applied layers.

According to one aspect of the invention, there is provided a method of producing a flexible structure that comprises a plurality of thin-film layers of elastomeric material and at least one layer of micro-wrinkled electrically conductive material, the method comprising:

a) applying a selective anti-adhesion treatment process to a carrier substrate whereby an outer peripheral region of the substrate provides a strong adhesion region and the area of the substrate within the outer peripheral region provides an anti-adhesion central region;

b) forming, on the carrier substrate, a first plurality of successive thin-film layers of PDMS, each of the successive thin-film layers of PDMS having a smaller ratio of crosslinking agent to base material and hence a higher Young's modulus than a preceding one of the thin-film layer of PDMS;

c) forming, on the last-formed thin-film layer of PDMS, a first thin-film layer of Parylene;

d) placing the carrier substrate in an organic solvent for a first period of time to induce swelling in the first plurality of thin-film layers of PDMS;

e) forming, on the first thin-film layer of Parylene a first further thin-film layer of PDMS;

f) forming by vacuum deposition, on the first further thin-film layer of PDMS, a second thin-film layer of Parylene in which a permanent micro-scale wrinkled surface morphology is generated as a consequence of diffusion of the organic solvent from the first plurality of thin-film layers of PDMS during said vacuum deposition, thus providing a first micro-scale wrinkled Parylene layer;

g) forming and patterning a first layer of electrically conductive material on the first micro-scale wrinkled Parylene layer such that the first patterned electrically conductive material has a micro-scale wrinkled surface morphology conforming to that of the first micro-scale wrinkled Parylene layer, thus providing a first micro-scale wrinkled electrically conductive pattern layer.

In some embodiments, the selective anti-adhesion treatment process applied to the carrier substrate comprises a process whereby the outer peripheral region of the substrate is made highly hydrophilic and the central area of the substrate within the outer peripheral region is made highly hydrophobic. The central area of the substrate may be made highly hydrophobic via desiccation of a thin anti-adhesive layer such as trichloro (1H,1H,2H,2H-perfluorooctyl-silane) . The outer peripheral region of the substrate may be made highly hydrophilic via selective $O_2$ plasma etching In some embodiments, the organic solvent and the first period of time are selected to induce a degree of swelling in the first plurality of thin-film layers of PDMS that causes the permanent micro-scale wrinkled surface morphology to be generated in the first further thin-film layer of PDMS. The organic solvent and the first period of time may be selected so as to obtain a desired wrinkling undulation wavelength of the permanent micro-scale wrinkled surface morphology generated in the first further thin-film layer of PDMS.

In some embodiments, the organic solvent is n-methyl-2-pyrrolidone, dioxane, dimethyl carbonate, pyridine or dimethylformamide.

In some embodiments, the first further thin-film layer of PDMS has a Young's modulus equal to that of the last-formed layer of the first plurality of thin-film layers of PDMS.

In some embodiments, the carrier substrate is a silicon wafer.

In some embodiments, a second micro-scale wrinkled electrically conductive pattern layer is formed by:

placing the carrier substrate in an organic solvent for a second period of time to re-induce swelling in the first plurality of thin-film layers of PDMS;

forming one or more additional thin-film layers of PDMS on the uppermost layer of the preceding structure;

forming by vacuum deposition, on the uppermost of the additional thin-film layers of PDMS, a third thin-film layer of Parylene in which a permanent micro-scale wrinkled surface morphology is generated as a consequence of diffusion of the organic solvent from the first plurality of thin-film layers of PDMS during said vacuum deposition, thus providing a second micro-scale wrinkled Parylene layer; and forming and patterning a second layer of electrically conductive material on the second micro-scale wrinkled Parylene layer such that the second patterned electrically conductive material has a micro-scale wrinkled surface morphology conforming to that of the first micro-scale wrinkled Parylene layer, thus providing a second micro-scale wrinkled electrically conductive pattern layer.

Some embodiments further comprise forming one or more additional layers of PDMS on the first micro-scale wrinkled electrically conductive pattern layer and patterning one or more of the one or more additional thin-film layers of PDMS to create a 3D microstructure. The 3D microstructure may be formed photolithographically. The patterning of the 3D microstructure may provide an array of individual 3D microstructures corresponding to an array of individual devices. One or more of the individual 3D microstructures may have one or more physical parameters that is different from one or more of the other individual 3D microstructures. A second micro-scale wrinkled electrically conductive pattern layer may be formed by the method of forming a second micro-scale wrinkled electrically conductive pattern layer mentioned above. The one or more additional thin-film layers of PDMS in that method may include the one or more additional thin-film layers of PDMS that are used to create the 3D microstructure. Placing the carrier substrate in the organic solvent for the second period of time to re-induce swelling in the first plurality of thin-film layers of PDMS may also dissolve a photolithographic photomask used for patterning the 3D microstructure. The 3D microstructure may comprise an array of individual frustum arrays and each of the first and second micro-scale wrinkled electrically conductive pattern layers may comprise an array of individual inductive structures, and each inductive structure of each micro-scale wrinkled electrically conductive pattern layer may be aligned with a corresponding frustum array of the 3D microstructure and a corresponding inductive structure of the other micro-scale wrinkled electrically conductive pattern layer to provide an array of individual devices usable as wireless LC sensors. Side-wall angles of the frustum array may be determined by UV exposure during photolithographic formation of the 3D microstructure.

Each layer of electrically conductive material may be patterned using photolithography.

The patterning of each layer of electrically conductive material may provide an array of individual electrically conductive structures corresponding to an array of individual devices. One or more of the individual electrically conductive structures may have one or more physical parameters that is different from one or more of the other individual electrically conductive structures.

Each layer of electrically conductive material may be a metallic layer. Each metallic layer may comprise one or more of Titanium, Aluminium, Chromium, Gold, Silver, Copper, Tungsten, Platinum and Lead. Each metallic layer may comprise a first layer of Titanium or Chromium and a second layer of Aluminium.

In accordance with a second aspect of the invention, there is provided a flexible structure that comprises a plurality of thin-film layers of elastomeric material and at least one layer of micro-wrinkled electrically conductive material, the structure comprising:
  a first plurality of successive thin-film layers of PDMS, each of the successive thin-film layers of PDMS having a smaller ratio of crosslinking agent to base material and hence a higher Young's modulus than a preceding one of the thin-film layer of PDMS;
  a first thin-film layer of Parylene;
  on the first thin-film layer of Parylene, a first further thin-film layer of PDMS;
  on the first further thin-film layer of PDMS, a second thin-film layer of Parylene having a permanent micro-scale wrinkled surface morphology, providing a first micro-scale wrinkled Parylene layer;
  a first layer of electrically conductive material on the first micro-scale wrinkled Parylene layer having a micro-scale wrinkled surface morphology conforming to that of the first micro-scale wrinkled Parylene layer, providing a first micro-scale wrinkled electrically conductive pattern layer.

The first further thin-film layer of PDMS may have a Young's modulus equal to that of the last-formed layer of the first plurality of thin-film layers of PDMS.

The structure may further comprise:
  one or more additional thin-film layers of PDMS on the uppermost layer of the preceding structure;
  a third thin-film layer of Parylene having a permanent micro-scale wrinkled surface morphology, providing a second micro-scale wrinkled Parylene layer; and
  a second layer of electrically conductive material on the second micro-scale wrinkled Parylene layer such that the second patterned electrically conductive material has a micro-scale wrinkled surface morphology conforming to that of the first micro-scale wrinkled Parylene layer, thus providing a second micro-scale wrinkled electrically conductive pattern layer.

The structure may further comprise one or more additional layers of PDMS on the first micro-scale wrinkled electrically conductive pattern layer, one or more of the additional layers of PDMS patterned to provide a 3D microstructure. The patterning of the 3D microstructure may provide an array of individual 3D microstructures corresponding to an array of individual devices. One or more of the individual 3D microstructures has one or more physical parameters that is different from one or more of the other individual 3D microstructures. The structure may include a second micro-scale wrinkled electrically conductive pattern layer. The one or more additional thin-film layers of PDMS may include the one or more additional thin-film layers of PDMS that provide the 3D microstructure. The 3D microstructure may comprise an array of individual frustum arrays and each of the first and second micro-scale wrinkled electrically conductive pattern layers may comprise an array of individual inductive structures. Each inductive structure of each micro-scale wrinkled electrically conductive pattern layer may be aligned with a corresponding frustum array of the 3D microstructure and a corresponding inductive structure of the other micro-scale wrinkled electrically conductive pattern layer to provide an array of individual devices usable as wireless LC sensors. Side-wall angles of the frustum array may be determined by UV exposure during photolithographic formation of the 3D microstructure.

Each layer of electrically conductive material may be patterned using photolithography.

The patterning of each layer of electrically conductive material may provide an array of individual electrically conductive structures corresponding to an array of individual devices. One or more of the individual electrically conductive structures may have one or more physical parameters that is different from one or more of the other individual electrically conductive structures.

Each layer of electrically conductive material may be a metallic layer. Each metallic layer may comprise one or more of Titanium, Aluminium, Chromium, Gold, Silver, Copper, Tungsten, Platinum and Lead. Each metallic layer may comprise a first layer of Titanium or Chromium and a second layer of Aluminium.

A device embodying the invention may comprise one of the array of individual devices mentioned above. The device may be a wireless LC sensor.

DESCRIPTION OF THE DRAWINGS

Embodiments of the invention will now be described, by way of example only, with reference to the accompanying drawings, in which:

FIGS. 3A to 3E illustrate a process of manufacturing an array of wireless LC sensors according to an embodiment of the invention.

FIG. 4 is a cross-sectional view of part of a sensor manufactured according to the method of FIGS. 3A to 3E.

FIG. 5A further illustrates a selective anti-adhesion pre-treatment process of a carrier wafer illustrated in FIG. 3A.

DETAILED DESCRIPTION OF EMBODIMENTS

Embodiments of the invention will be described herein with particular reference, by way of example, to a flexible wireless LC pressure sensor. The invention is applicable to other types of sensor and other devices, as discussed in the following description. Preferred embodiments provide for wafer-scale production of arrays of sensors/devices, employing a silicon wafer as a carrier substrate for the bottom-up production of flexible, multi-layer thin-film structures that can incorporate micro-wrinkled electrically conductive elements and three-dimensional microstructures. The invention enables the simultaneous production of an array of multiple thin-film sensors/devices on a wafer, in which physical parameters of individual sensors/devices in the array may vary between sensors/devices. References to "wafers" in the following description will be understood to refer to a silicon wafer as the preferred carrier substrate for the methods described. References to "arrays" will be understood to refer to an array of sensors/devices formed on such a carrier substrate, and general references to "films" will be understood to refer to composites of thin-film layers that provide the basis for the arrays of sensors/devices.

Figure 1A:
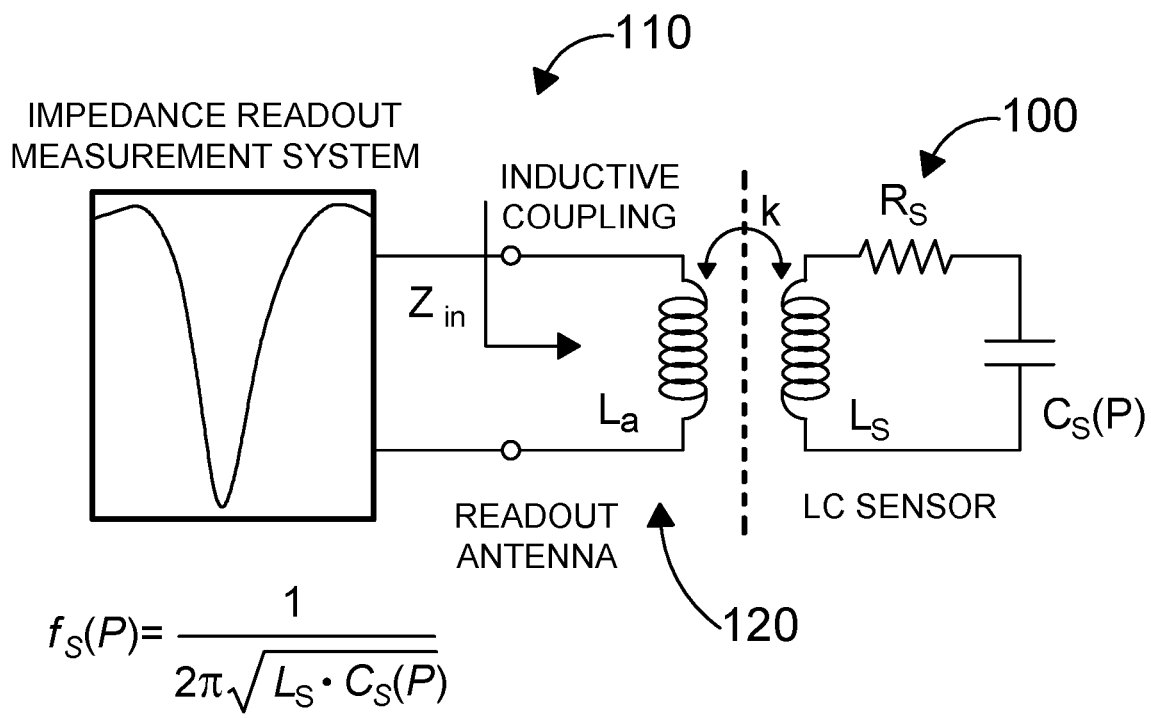
FIG. 1A is a circuit diagram illustrating the principle of operation of a wireless LC pressure sensor of a type that may be implemented using the invention.

Referring now to the drawings, FIG. 1A is a circuit diagram illustrating the principle of operation of a wireless LC pressure sensor of a type that may be implemented using the invention.

The general LC sensor circuit 100 comprises an inductance, $L_s$, a resistance $R_s$ and a capacitance $C_s$. The physical structure of the sensor is such that $C_s$ varies with pressure applied to the sensor, so that the resonant frequency of the sensor circuit 100 also varies with pressure.

This circuit is the general operational circuit for LC sensors. The double-inductor LC structure of the sensor described below can be shown to be equivalent to the circuit of FIG. 1. $L_s$ and $C_s$ are the effective (coupled) inductance and capacitance of two aligned inductors of the structure.

A wireless readout measurement system 110 includes a readout antenna 120 including an inductance $L_a$ that can be inductively coupled to the sensor inductance $L_s$. The readout system 110 measures the resonant frequency of the sensor circuit, so as to determine the pressure applied to the sensor.

The resonant frequency of the sensor circuit can be measured, for example, by exciting the LC circuit by a frequency sweep of radio-frequency (RF) energy and then using a phase detector to locate the resonant frequency, or by exciting the LC circuit by a burst of RF energy at a predetermined frequency or set of frequencies and using a phased-locked-loop (PLL) circuit to lock onto the sensor's resonant frequency.

Figure 1B:
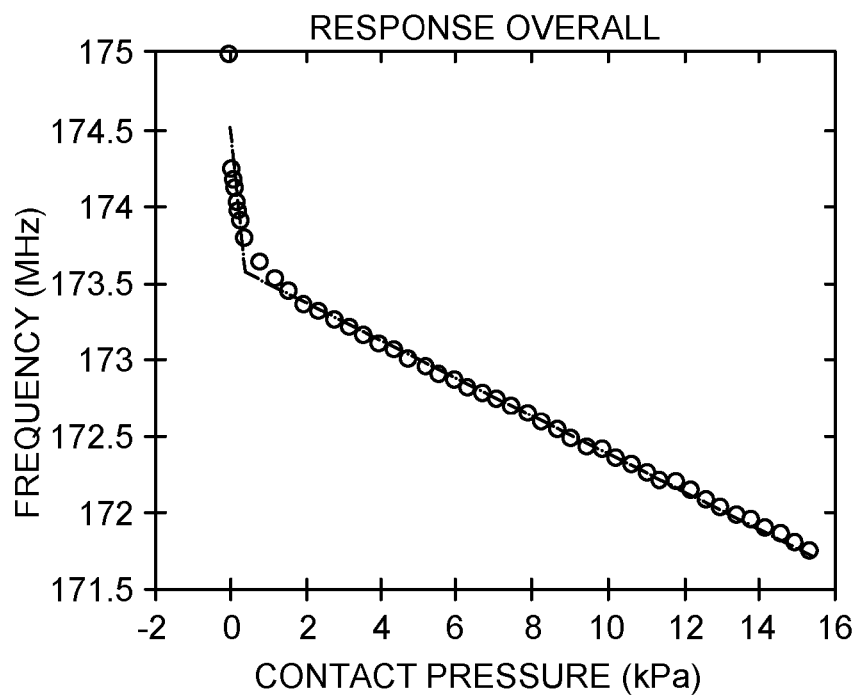
FIG. 1B is a graph showing an example of how the resonant frequency of a LC pressure sensor varies with contact pressure.

FIG. 1B is a graph showing an example of how the resonant frequency of a LC pressure sensor varies with contact pressure.

Wireless LC pressure sensors and readout systems of these general types are well known to those skilled in the art and will not be described in detail herein except as necessary for the purpose of understanding the present invention, which provides improved methods of manufacturing such wireless LC sensors and improved sensors obtained by those methods.

Figure 2:
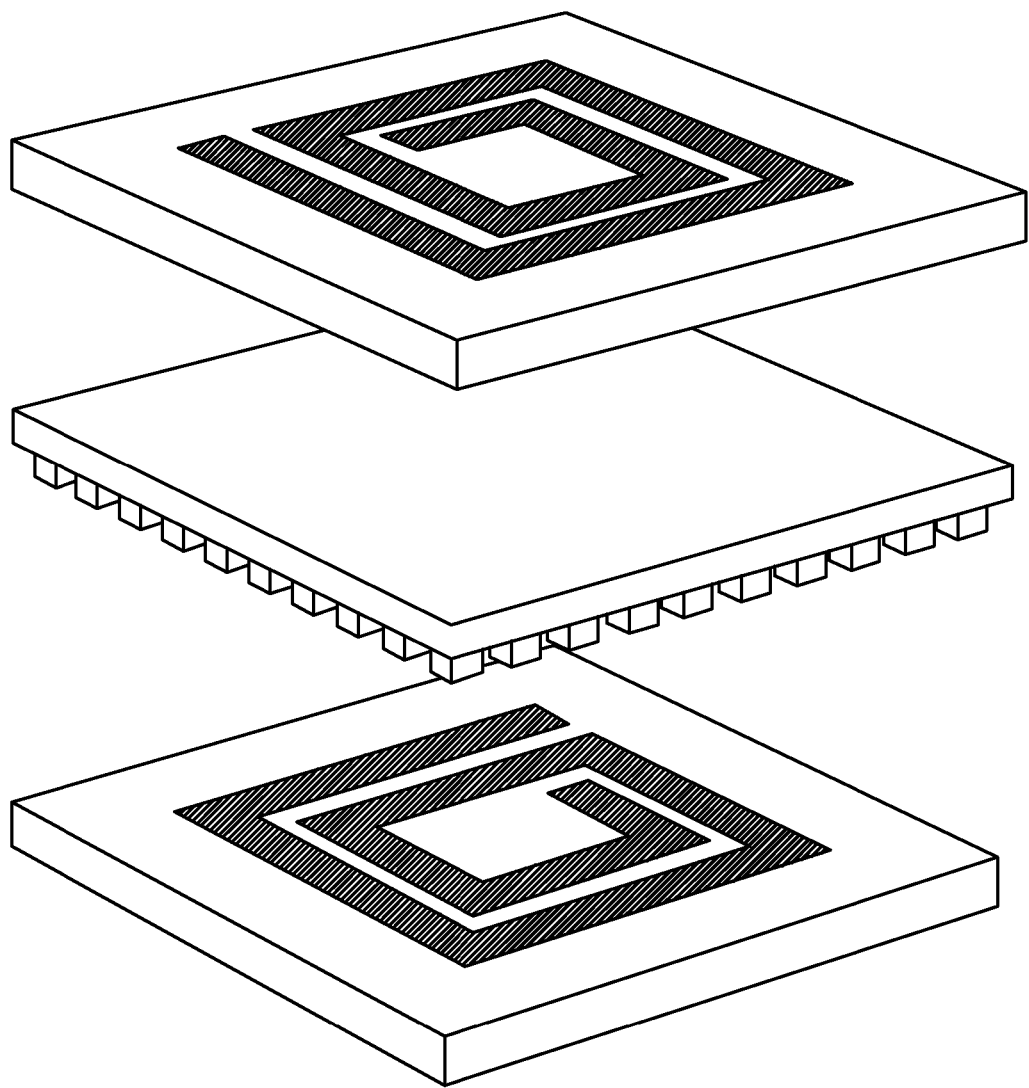
FIG. 2 is an exploded view illustrating the physical structure of a type of wireless LC pressure sensor 200 that can be implemented using the present invention.

FIG. 2 is an exploded schematic view illustrating the physical structure of a type of wireless LC pressure sensor 200 that can be implemented using the present invention. The structure comprises a bottom layer 210 incorporating a first inductive structure 220, a middle layer 230 incorporating a sensor microstructure 240 and a top layer 250 incorporating a second inductive structure 260 aligned with the first inductive structure 220. The first and second inductive structures 220 and 260 together provide the inductance and capacitance of the sensor 200, the latter stemming from the overlapping tracks of the two aligned inductive structures 220 and 250, with the middle layer 230 acting as the dielectric of the coupled capacitor. The physical properties of the sensor microstructure 240 are such that the thickness and relative permittivity of the middle layer varies with compressive deformation, e.g. applied pressure. Primarily the reduction of thickness of the microstructured layer in response to compressive deformation is the dominant factor.

The microstructure 240 may, for example, be a structured elastomer comprising a frustum array such as an array of pyramidal structures. The thickness and relative permittivity of the middle layer 230, and the manner in which it varies with pressure, depends in part on the materials used and in part on the physical characteristics of the microstructure 240. Thus, for a given material, the frequency response of the sensor 200 depends on the physical parameters of the frustum array, such as the size, shape (including wall angles) and spacing/density of the frusta. Aspects of the present invention allow these parameters, including frustum wall angles, to be controlled so as to fine tune the frequency response and sensitivity of the sensors to compressive deformation, and to allow different sensors in an array of simultaneously produced sensors to have different frequency responses.

In regard to this latter point, the overall process as described herein enables:

(1) The production of uniform microstructured layers that are tunable in terms of structural and array configuration parameters, which affect overall the sensors' mechanical response to compression (i.e. the microstructuring process described below). The direct photolithographic approach that is employed herein to form an embedded microstructured layer directly onto a thin-film substrate allows in principle the microfeatures of the microstructured layer to be designed selectively for individual sensors in an array of sensors that are produced simultaneously (i.e. by incorporating variations between individual sensors into the photolithographic photomask design). Variable feature geometries may be applied across the array either per sensor or per sensor array region; e.g. base dimensions of the frusta, spacing/density of the frusta, frustum geometry (circular, square, triangular, rectangular etc.). The thickness and frustum angle, although both fully tunable, may be kept uniform across the array and hence be the same for all sensors per wafer batch. All the above control the mechanical (structural) response of the sensors to deformation, along with the physical parameters of microstuctured layer material (eg. Young's modulus, ie. elasticity)

(2) Ultra-dense scalable LC sensor arrays (eg. 200 μm spacing as demonstrated herein), where each sensor can be designed (inductor size, track dimensions such as loops, width and spacing) to operate in a unique resonant frequency domain; i.e. to provide uniquely addressable sensors, by virtue of the wrinkling/metallisation and assembly processes employed. There is inherently a fundamental relationship between the ambient resonant frequency of an LC sensor (ie. operational frequency regime) and the sensitivity to pressure which can be leveraged also.

(3) The combination of (1) and (2) above (i.e. the overall process) allows fully tunable sensor arrays in terms of performance, operating frequency domain and sensor size.

Figure 11:
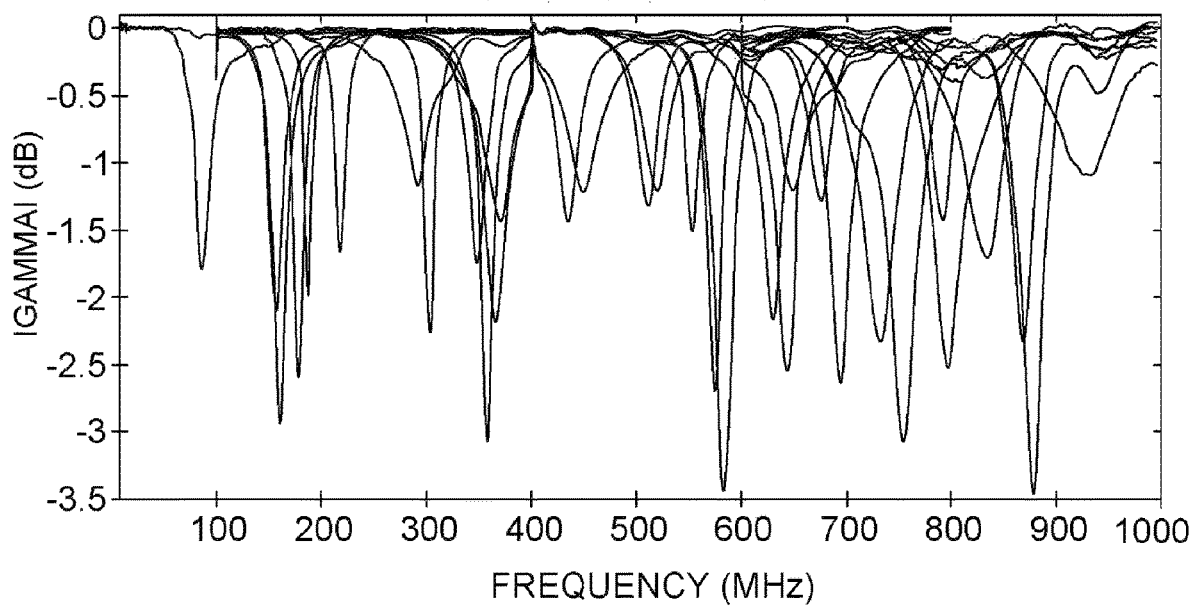
FIG. 11 is a graph demonstrating sensors developed in one batch with unique resonant frequencies covering the 80 MHz to 1 GHz frequency band.

Furthermore, the overall process allows double-inductor LC sensors to be developed to operate, if desired, at an advantageous low frequency band of <80 MHz to 1 GHz, as shown in FIG. 11, in contrast to prior art double-inductor LC sensors that operate >1 GHz, which is more suitable for use in medical applications (i.e. affected less by tissue attenuation). The present invention, however, may also be used to produce double-inductor LC sensors that operate >1 GHz.

The layers 210, 230 and 250 and microstructure 240 are formed from optically transparent elastomeric materials so that the sensor structure is flexible and permits alignment of features formed by photolithographic techniques as described below. The present invention employs PDMS (polydimethylsiloxane, also known as dimethylpolysiloxane or dimethicone) and Parylene (preferably Parylene C), as discussed in detail below.

The inductive structures 220 and 260 may be formed from any suitable metallic or otherwise electrically conductive material, preferably a combination of nm-thin Titanium (Ti) or Chromium (Cr), acting as a seed layer to provide improved adhesion to the underlying substrate, and microscale thick Aluminium (Al) forming the bulk of the conductive layer, as in the embodiments of the present invention described below.

Other materials that are most suitable for inductive structures of these types include, e.g., Chromium, Gold, Silver, Copper, Tungsten, Platinum, Lead, etc., i.e. materials with a low resistivity coefficient of $p<\sim20*10^{-8}$ $\Omega$m that can enable a sufficiently high-quality factor for the LC sensors for effective wireless readout.

The inductive structures 220 and 260 typically comprise flat spiral structures, illustrated as being right-angled spirals although other spiral types may be employed such as other forms of polygonal spirals or circular/elliptical spirals. The shapes, sizes, thicknesses and materials of the inductive structures can be selected to provide whatever electrical properties are required and the materials may also be selected to provide required physical properties, particularly flexibility.

Besides LC pressure sensors, other sensor/device types that could potentially utilise the present invention include but are not limited to:

Gas/liquid sensor, e.g. "electronic-nose" or "e-nose". Introducing the sensor to a liquid or gaseous environment will allow the liquid/gas to enter a microstructured layer of the sensor, since the cross-section is exposed following singulation of the sensors from the film. Monitoring of the target quantity can be provided by either a change of the dielectric constant of the microstructured layer or/and by swelling (increase of thickness) since a number of solvents can induce significant swelling to PDMS such as chloroform, tetrahydrofuran, ether, xylenes, pentane, benzene etc.

Proximity sensor. When the sensor comes into proximity to a highly conductive material and vice versa, e.g. metal, the resonant frequency shifts upwards.

Bending and strain sensor. Bending or strain also induce compressive deformation and the sensor can be potentially repurposed for such applications.

Flexible antennas/electronics. The microscale wrinkled low resistivity metallisation and thin-film flexible biocompatible PDMS substrate described herein lends itself for the development of high performing flexible antennas (eg. wearable or biomedical applications) or as a more flexible substitute to polyimide for flexible electronics.

As described further below, the present invention includes methods of producing microscale wrinkled ("microwrinkled") electrically conductive layers, that can be used for providing the inductive structures of a wireless LC sensor, to enable a high degree of flexibility.

Referring now to FIGS. 3 to 5, one aspect of the invention provides a process for manufacturing flexible thin-film structures providing devices such as wireless LC sensors and, more particularly, for manufacturing an array of multiple discrete devices/sensors on a single carrier substrate (wafer) where the devices/sensors of the array can each have differing characteristics.

Figure 5B:
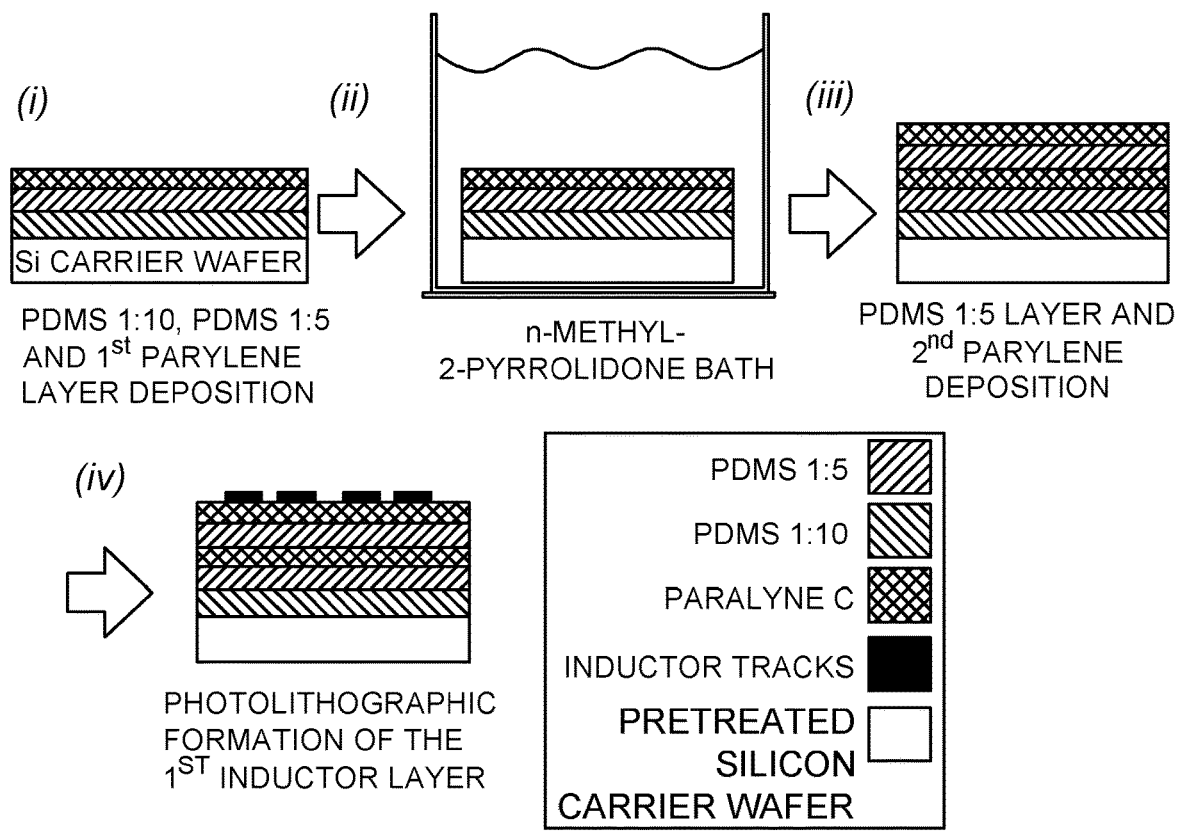
FIG. 5B further illustrates a perma-frosted wrinkled metallisation process illustrated in FIG. 3B.
Figure 5C:
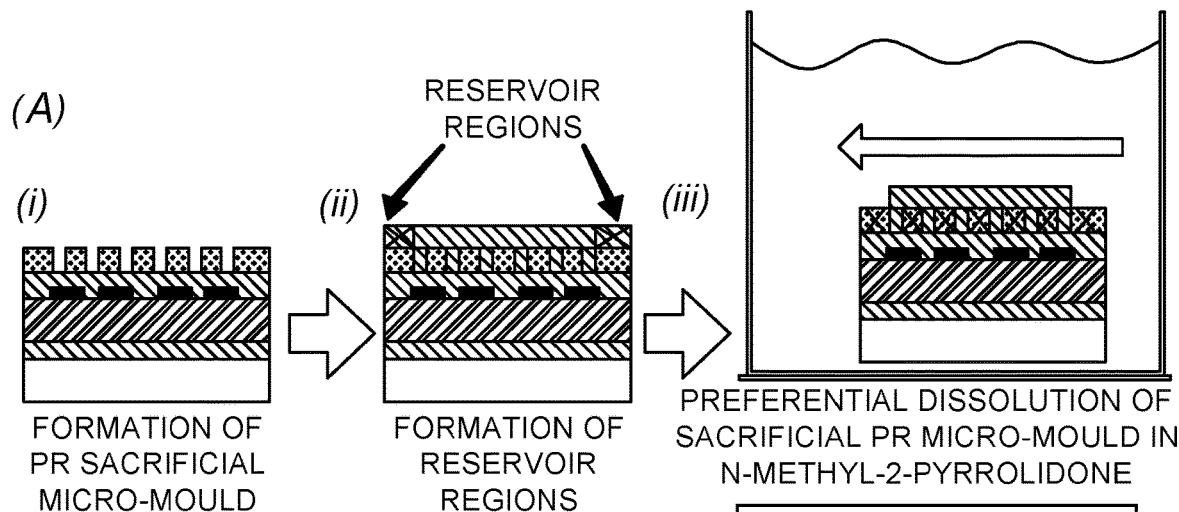
FIG. 5C further illustrates a microstructure microfabrication process illustrated in FIG. 3C.

FIGS. 3A to 3E provide an overview of an example embodiment of a process for producing wireless LC sensors, FIG. 4 shows a cross section of the sensor structure that is produced, and FIGS. 5A to 5C illustrate further details of sub-processes shown in FIGS. 3A to 3D.

The overall process involves bottom-up deposition of successive layers of different materials on a carrier substrate such as a silicon carrier wafer 310. A preferred embodiment includes a selective anti-adhesion treatment process applied to the surface of the carrier wafer 310 as seen in FIG. 3A, whereby the periphery 320 of the wafer is made hydrophilic, to provide strong adhesion, and the central area 330 is made hydrophobic, to provide low adhesion. This preliminary process is described in more detail below, with reference to FIG. 5A. It will be understood that FIGS. 3 to 5, for the purposes of illustration, show a small section of a single sensor structure whereas the carrier wafer 310 with its hydrophilic periphery 320 and hydrophobic central area 330 would carry an array of multiple individual sensors.

FIG. 3B shows the sensor structure after a first set of layers have been deposited successively on the carrier wafer 310; i.e. layers L1 to L6 of FIG. 4 as detailed in Table 1 below. Layers L1 to L5 together correspond to the bottom layer 210 of FIG. 2 and layer L6 corresponds to the first inductive structure 220 of FIG. 2.

FIG. 3C shows the sensor structure after a second set of layers have been deposited on top of the preceding layers; i.e. layers L7 to L9 of FIG. 4 and as detailed in Table 1 below. Layer L7 encapsulates the first inductive structure (layer L6) and layers L8 and L9 correspond to the middle layer 230 and sensor microstructure 240 of FIG. 2.

FIG. 3D shows the sensor structure after a third set of layers have been deposited on top of the preceding layers; i.e. layers L10 to L12 of FIG. 4 and as detailed in Table 1 below. Layers L10 and L11 together correspond to the top layer 250 of FIG. 2 and layer L12 corresponds to the second inductive structure 260 of FIG. 2.

FIG. 3E shows the final sensor structure after being dried out, final layer L13 deposited to encapsulate the second inductance structure (layer L12) and the sensor array having been peeled off from the carrier wafer 310.

As shall be described further below, the invention employs layers of PDMS and Parylene (preferably Parylene C) of differing elasticities so as to provide Parylene surfaces that are uniformly wrinkled in two dimensions ("2D wrinkled surfaces") on the microscale ("microscale wrinkling" or "micro-wrinkling"), on which the metal layers L6 and L12 are deposited so that the metal layers are themselves micro-wrinkled and therefore highly flexible.

One particular embodiment of a wireless LC sensor in accordance with the invention comprises layers L1 to L13 as set out in Table 1 below.

TABLE 1

| Layer | Material | Young's Modulus | Morphology | Thickness (μm) |
|---|---|---|---|---|
| L1 | PDMS 1:10 | 1.7 MPa | Uniform | 19 |
| L2 | PDMS 1:5 | 3.2 MPa | Uniform | 19 |
| L3 | Parylene | 2.7 GPa | Uniform | 2.5 |
| L4 | PDMS 1:5 | 3.2 MPa | uniform | 19 |
| L5 | Parylene | 2.7 GPa | wrinkled | 2.5 |
| L6 | Ti/Al | | wrinkled | [1-2]* |
| L7 | PDMS 1:10 | 1.7 Mpa | uniform | 19 |
| L8 | PDMS 1:10 | ≤1.7 Mpa | 50 × 50 μm² elements | 13 |
| L9 | PDMS 1:10 | ≤1.7 Mpa | uniform | 19 |
| L10 | PDMS 1:5 | 3.2 Mpa | uniform | 19 |
| L11 | Parylene | 2.7 GPa | wrinkled | 2.5 |
| L12 | Ti/Al | | wrinkled | [1-2]* |
| L13 | PDMS 1:5 | 3.2 Mpa | uniform | 19 |
| Total | | | | 153.5* |

*NOTE the total thickness of the sensor structure does not include the thicknesses of the metal layers L6 and L12, which are encapsulated in the thicknesses of layers L7 and L13.

As can be seen from the table, the sensor structure includes thin-film elastomer layers of (i) PDMS using two different ratios of crosslinking agent to base material, thus having different elasticities: PDMS 1:10 for layers L1 and L7-L9 (Young's modulus 1.7 MPa, or greater for L8 and L9, which constitute the middle layer 230/microstructure 240 of the sensor 200) and PDMS 1:5 (Young's modulus 3.2 MPa) for layers L2, L4, L10 and L13, and (ii) Parylene, layers L3, L5 and L11 having a much higher Young's modulus (2.7 GPa).

The invention employs thin-film PDMS layers of progressively increasing hardness (increasing Young's modulus), creating a gradient of reducing elasticity in the direction towards the Parylene layers (L5 and L11 in this example) that exhibit micro-scale wrinkling in the finished product. The elasticity gradient contributes to the formation of the micro-scale wrinkled surface as described further below. As a minimum, two such PDMS layers are needed to create the required elasticity gradient. The use of this minimum number of two PDMS layers is preferred in order to minimise the complexity of the structure and hence the time and cost of production.

PDMS elasticity can be varied in two ways, as long as a gradient Young's modulus is sustained towards the upper layer interface to be metallised to allow the wrinkling to emerge (see description of wrinkling method below):
1. Elastomer base to crosslinking agent of native PDMS, eg Sylgard 184, from 1:50 to 1:5 results to a Young's modulus of 10 kPa to 3.5 MPa respectively (dependant also on the curing temperature and curing time)
2. PDMS blends, such as Sylgard 527 and Sylgard 184, result in a more controlled and stable Young's modulus of 5 kPa to 1.7 MPa (i.e. avoids partial crosslinking and unwanted diffusion that may arise when the ratio is reduced significantly)
3. The Young's modulus affects the mechanical response of the sensor to compressive deformation, which is especially important for the L8 (microstructured) layer, and further relates to the tuning capacity of the sensor performance.

In this example the PDMS layers all have a thickness of 19 μm, except layer L8 (microstructured layer) with a thickness of 13 μm, while the Parylene layers are much thinner, 2.5 μm.

Spin-coating of PDMS and vacuum deposition for Parylene enable precision control and uniformity of the thickness of the layers across the wafer. The use of vacuum deposition for the Parylene layers also plays a role in the wrinkling of Parylene layers L5 and L11, as described below.

For the PDMS layers, thickness can be varied from <10 µm to >200 µm via spin coating.

Thin-film elastomers allow higher conformability (bending) and thus improved flexibility. Increasing the thickness t of the layers, especially for layers L6-L10, reduces significantly the capacitance of the sensor and the inductive coupling of the two inductors of the sensor, resulting in a proportional increase of their resonant frequencies (ie. ~√t). Furthermore, for layers L6-L10, a substantial overall thickness increase (eg. t>500 µm, i.e. not a thin film any more) would effectively nullify the inductive and capacitive coupling of the two aligned inductors of the sensor structure resulting in a decoupled sensor system that is electromagnetically insensitive to compressive deformation.

For the Parylene layers, the thickness can be controlled by the rate of deposition of the equipment (eg. SCS PDS2010 parylene coater).

0.5 µm to 3 µm tested thicknesses exhibited no observable impact to the sensors' flexibility and performance.

Thicknesses <0.5 µm are expected to result in insufficient coverage of the substrate's surface for effective metallisation, while thicknesses >5 µm are likely to result in an over-coverage, burying the wrinkled surface and resulting instead in planar morphologies. Planar surfaces lead to crack formation under bending or compressive deformation (discussed further below in reference to the wrinkling method).

In this example the microstructure frustum array provided by layer L8 comprises 50×50 µm² elements.

The microstructured layer is formed photolithographically (ie. via spin coating and UV exposure of a sacrificial micromould photoresist layer). As such, the features' dimensions, geometry or/and spacing can be varied with precision from <1 µm to as large as desired e.g. >1 mm (i.e. dependent on photomask design and UV exposure system).

The geometry of the microstructure array can be varied also to include square microfeatures, or circular, triangular, rectangular etc. or any combination thereof, with or without different/variable structural dimensions (i.e. dependent on the photomask design). The latter can enable tunable and selective mechanical response of individual sensors or sensor array regions of the film depending on the requirements (discussed further below in reference to the microstructuring process).

As shall be discussed further below, the manufacturing process results in Parylene layers L5 and L11, and thus the metal layers L6 and L7 deposited thereon, having a micro-wrinkled surface morphology, while the other layers have a uniform surface morphology.

FIG. 5A further illustrates the selective anti-adhesion treatment process of FIG. 3A, whereby the main central area 330 of the Si carrier wafer 310 is made selectively highly hydrophobic, for example via desiccation of a thin layer of trichloro (1H,1H,2H,2H-perfluorooctyl-silane), thereby providing an active anti-adhesion central region. The use of any corresponding low surface tension layer to achieve reduction of adhesion in the central region may be employed to provide a similar result. The wafer outer periphery 320 is made highly hydrophilic, for example via selective $O_2$ plasma etching, thereby providing a supportive strong adhesion region.

The width of the outer peripheral region 320 relative to a diameter of the carrier substrate 310 is selected to be as small as possible while ensuring that adhesion of the first layer of the first PDMS layer L1 to the substrate is maintained during subsequent process steps. It is desirable for the radial width of the strongly bounded area to be as small as possible as this provides more usable effective area for the sensor arrays to be developed. In the example process described herein, utilising 3 inch (7.62 cm) wafers, the width was arbitrarily chosen to be around 10 mm to ensure a strong bounding of the elastomer film to the carrier wafer and strong planarity of the film during processing, but this width could be reduced, possibly to as low as 0.5-1 mm, if desired.

Uniform deposition on the surface of the Si wafer of a nanometre thin layer of trichloro (1H,1H,2H,2H-perfluorooctyl-silane) (3 droplets in vial) may be accomplished through adsorption in a desiccator for 3 h (active anti-adhesion region). The selective O2 plasma etching of the outer periphery of the wafer surface may be facilitated by the attachment of a temporary mask on the wafer that shields the central anti-adhesion area.

The selective anti-adhesion treatment provides strong boundary conditions for the emergence of highly uniform and isotropic undulations (typically of wavelength λ on the order of 7.5 µm) of the two-dimensional wrinkled surface morphology across the whole surface area of the wafer for the subsequent wrinkled metallisation process, while later enabling manual delamination (detachment) of the sensor film from the carrier wafer 310, and further enabling high planarity of the film during processing.

The role of this anti-adhesion process in providing uniform and isotropic wrinkling across the whole surface during the later stages is described further below.

FIG. 5B illustrates the wrinkled metallisation process for the first inductor layer L6, which comprises:

5B-(i)-a Deposition via spin-coating and thermal cross-linking successively of two thin film PDMS layers, L1 and L2, each with a different Young's modulus (in this example 1:10 and 1:5 PDMS crosslinking agent to base ratios respectively, for example using Sylgard™ 184 from The Dow Chemical Company).

Spin-coating of PDMS is the most reliable way to provide a controllable thin-film (ie. µm-scale) thickness on a wafer-scale. Alternatively, the typical casting methods used with PDMS leads to sub-mm to mm scale thick layers with little control on the film thickness and uniformity/planarity of the surface (see also discussion above regarding the importance to the sensor performance of having a thin-film structure). An alternative could be a spray jetting (coating) method, however this would require dilution (eg. hexane) to lower the viscosity of the material to be used with an airbrush (i.e. to pass through the nozzle) and would lower the hardness of the polymer.

5B-(i)-b Deposition via vacuum evaporation of a first thin-film Parylene C layer, L3.

Parylene coating is typically applied at ambient temperatures through a vapor deposition process (ie. with the use of specialized vacuum deposition equipment such as CS PDS 2010, Kisko) onto the substrate or material that is being conformally coated. Parylene polymer deposition takes place effectively at the molecular level, where films essentially 'grow' a molecule at a time.

5B-(ii) Placement of the wafer in a n-methyl-2-pyrrolidone bath for 12 hours. The purpose of this step is to induce low-intensity swelling in the PDMS layers L1 and L2, which in combination with the elasticity gradient referred to above leads to spontaneous wrinkling of Parylene layer L5 when it is subsequently applied. This is discussed further below.

Other biocompatible organic solvents with similar properties may be used (eg. with low swelling ratio S<1.1 and similar solubility—δ~11 cal$^{1/2}$cm$^{-3/2}$—to PDMS), such as dioxane, dimethyl carbonate, pyridine or dimethylformamide, (for such other solvents the time of placement in the solvent bath may be adjusted according to the S and δ parameters, so as to to obtain a wrinkling undulation wavelength of λ~7.5 μm as discussed herein).

5B-(iii)-a Deposition via spin-coating and crosslinking of a 1:5 ratio PDMS thin film layer, L4.

5B-(iii)-b Deposition via evaporation of a thin-film Parylene C layer, L5, and spontaneous generation of a permanently "frosted" and uniform two-dimensional wrinkled surface morphology (aided by the selective anti-adhesion treatment process described above), discussed further below.

Figure 6:
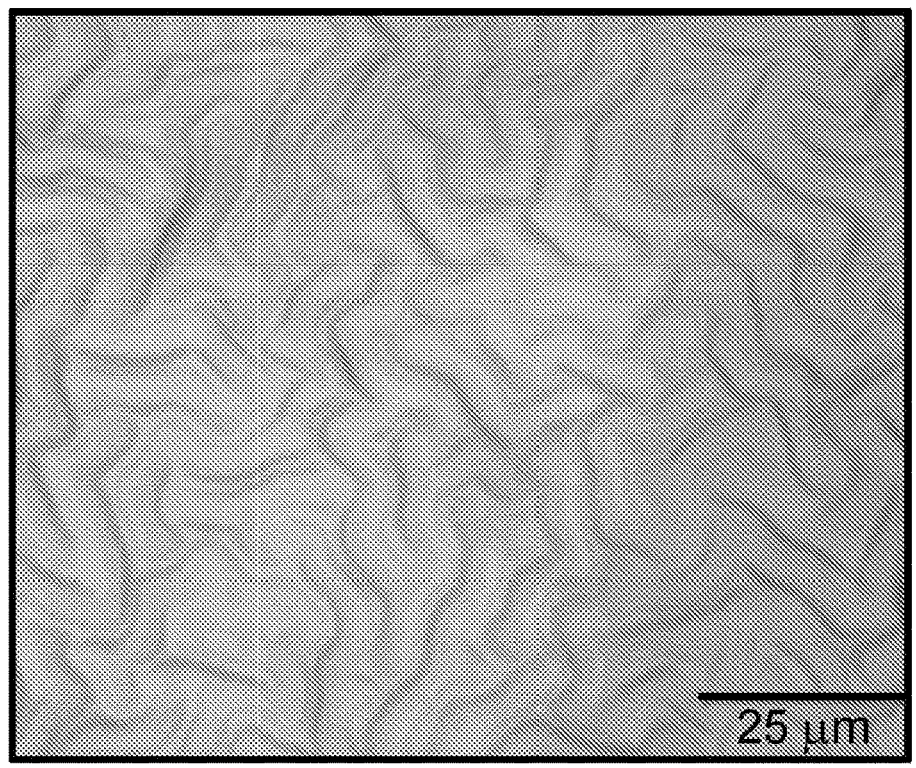
FIG. 6 shows a perma-frosted wrinkled surface of a Parylene-coated PDMS layer prior to metallisation.
Figure 7A:
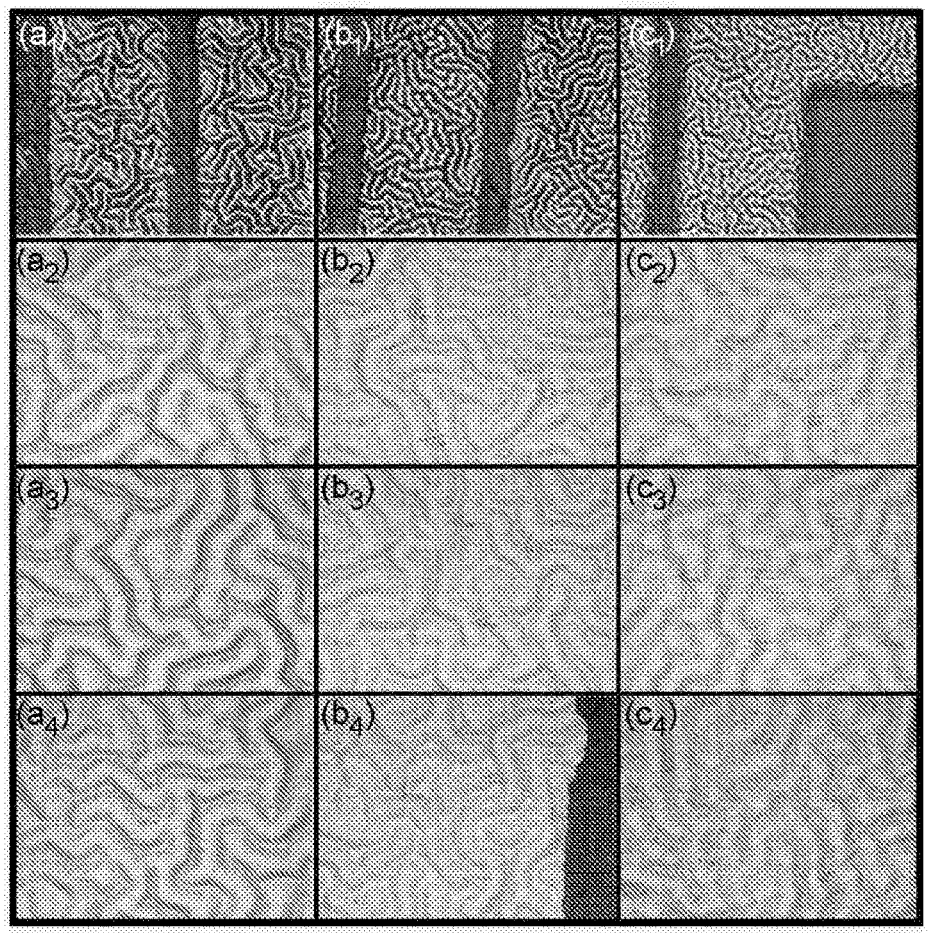
FIG. 7A shows examples of tunable microscale metallisation on a perma-frosted wrinkled surface of a Parylene-coated PDMS layer and the uniformity of the wavelength of undulations, where the letters correspond to a=1 µm, b=1.5 µm and c=2 µm metal deposition and the number subscripts (eg. $a_1$) to different wafer batches.
Figure 7B:
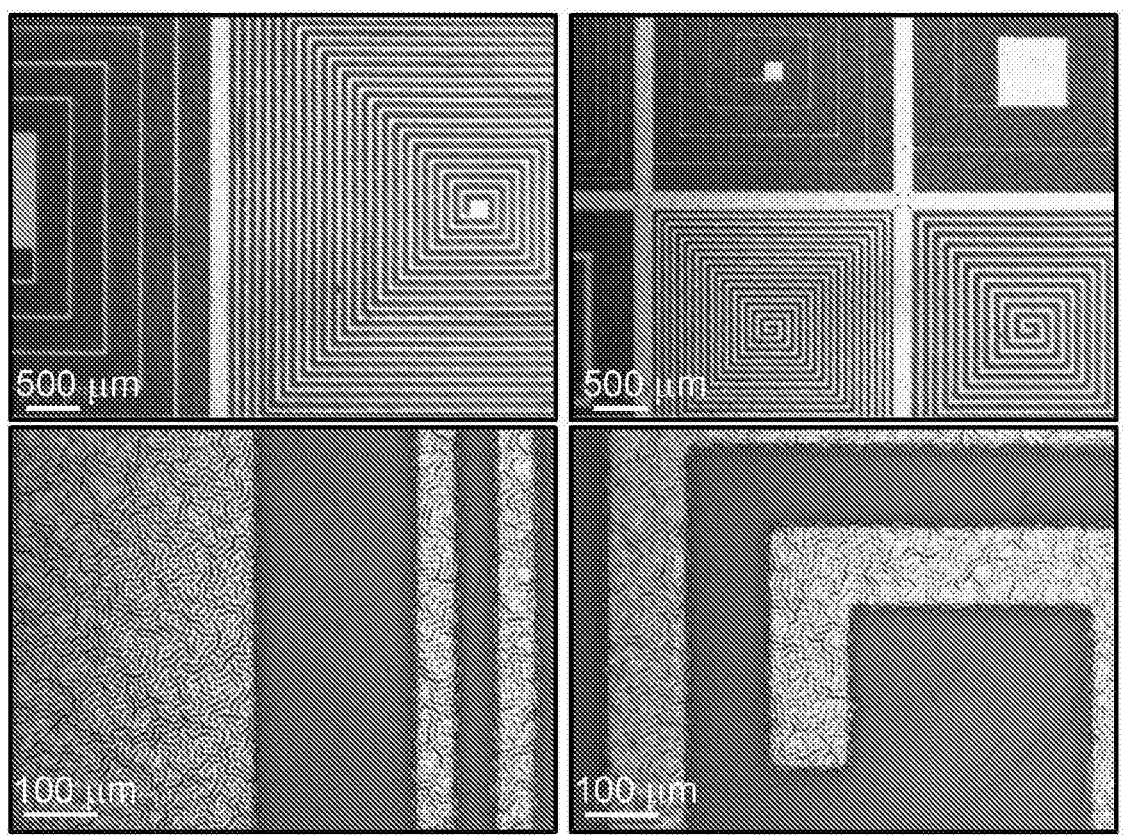
FIG. 7B illustrates the uniformity of the wrinkled metallisation (here 2 µm-thick) at a larger scale.
Figure 13:
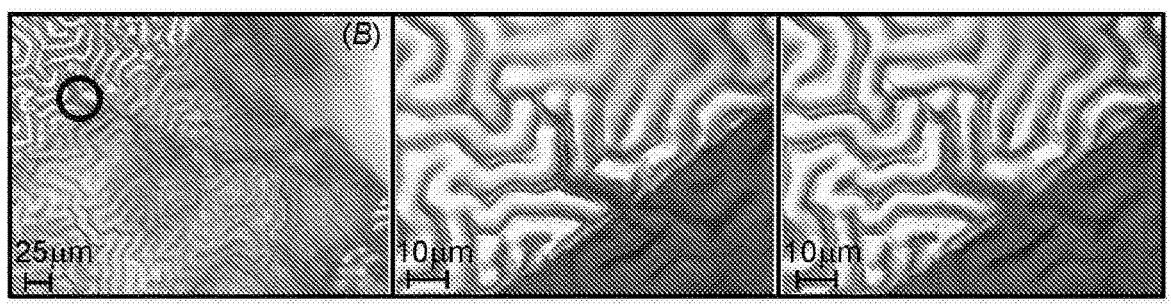
FIG. 13 illustrates the stress relief provided by the wrinkling whereas the induced cracking by a blade is stopped and contained only within a few micrometres near the site of damage.

NOTE: The terms "frosting", "frosted" and "permafrosted" are used herein to refer to stable, permanent microwrinkling, by analogy to frost patterns similar to the microwrinkling of the present invention as illustrated in FIGS. 6, 7 and 13. 5B-(iv) O$_2$ plasma etching and activation, photolithographic patterning of the first inductor structures, metallisation of the desired Ti/Al thickness via sputtering or e-beam evaporation (or, for example, electroplating or thermal evaporation) and lift-off dissolution to form the 1st inductor layer L6.

O$_2$ plasma etching increases adhesion of the metal to the Parylene surface; an alternative is O$_2$ reactive ion etching (RIE).

5B-(v) Encapsulation with a 1:10 thin-film PDMS layer L7 via spin-coating.

The structure created thus far, comprising layers L1 to L6, provides a flexible elastomeric substrate, consisting of layers L1 to L5, with a flexible micro-wrinkled electrically conductive layer L6 which may be patterned to provide an inductive spiral, as in the embodiments described herein, or any other useful conductive pattern; for example to provide a flexible antenna for wearable and/or biomedical applications. Layers L1 to L6 thus provide a novel and useful flexible structure independently of the additional layers L8 to L13 of these embodiments, and with or without a layer such as L7 encapsulating the conductive layer L6.

The spontaneous generation of the surface wrinkling of Parylene layer L5 on the PDMS substrate emerges due to a complex mechanical buckling instability at the upmost interface of the substrate, which is facilitated, in synergy, by both the gradient mechanical properties of the multi-layered substrate film and low intensity swelling induced by the n-methyl-2-pyrrolidone to the underlying layers (S=1.03 swelling coefficient for PDMS), and which is supported by the strong adhesion of the periphery of layer L1 to the carrier substrate.

The low intensity swelling of the non-homogenous multi-layered substrate results in a volume phase transition of the underlaying PDMS L1 and L2 layers that are constricted between the conformal coating provided by the L3 Parylene layer and the strong adhesion to the periphery of the rigid carrier wafer, and which in turn undergo an abrupt volume change as the swollen state is relaxed during the deposition of the L5 Parylene layer under vacuum, due to diffusion of the solvent from layers L1 and L2. The gradient variation of the mechanical properties of the non-homogeneous PDMS substrate (L1 and L2) and abrupt volume change due to diffusion of the solvent generate as a result an anisotropic osmotic pressure across the bulk of the film thickness, resulting in the emergence of in-plane equibiaxial compressive strains at the upmost (L4) PDMS layer interface that lead to buckling of the film and hence a labyrinthine wrinkling pattern ("frosting") of the surface, whilst the Parylene deposition (L5) concurrently aids in the stabilisation (frosting) of the wrinkle formation. The L3/L4 interface acts as a "stiff-soft" interface promoting the mechanical buckling instability, generated at L1/L2, towards the upmost "soft-stiff" interface L4/L5 and the emergence of the surface wrinkling The spontaneous wrinkling effectively acts as a self-organising mechanism across the film surface that minimizes the combined bending energy of the upmost layers' interface and the stored elastic strain energy of the inner layers. Control of the wrinkled morphology described herein (eg. wavelength of undulations) can be attained by tuning the mechanical properties (eg. Young's modulus) of the constituent layers of the substrate, the thickness of the layers, and/or the immersion time to the swelling-inducing organic solvent. This method is to be contrasted with the typical large intensity swelling methods of homogenous elastomer films (i.e. of a single native layer) reported in prior art that are limited by their inability in obtaining ordered wrinkled surfaces on a large scale since the large strains imposed by the solvents favour instead the formation of creases and folds (see, for example, J. Rodriguez-Hernandez, "Wrinkled interfaces: Taking advantage of surface instabilities to pattern polymer surfaces", *Progress in Polymer Science*, 2015, 1-41).

The uniformity of the wavelength of undulations (ie. λ~7.5 μm for the parameters reported herein) across the substrate surface is facilitated by the selective anti-adhesion pre-treatment of the wafer, which effectively creates strong bounded conditions on the periphery of the carrier wafer, and hence a firm interface between the elastomer base and the rigid surface of the wafer that leads the compressive strain sustained by the substrate during the conformal Parylene deposition (L5) to be directed towards the upmost interface. Parylene layer L5 concurrently provides the permanent frosting of the wrinkled morphology in combination to the above, as shown in FIG. 6, and enables the formation subsequently of crack-free metal tracks of a tunable microscale thickness, with the frosted wrinkling morphology retained irrespective of the deposited metal thickness, as shown in FIG. 7 (ie. in contrast to direct metal deposition to PDMS), since Parylene minimises the thermal expansion of the interfacial surface during the metal deposition. The latter stems directly from the thermal coefficient (α=3.5×10$^{-5}$ K$^{-1}$) of Parylene that is respectively 1 order of magnitude higher than that of PDMS (α=2×10$^{-4}$ K$^{-1}$) and closer to that of metals, such as for example, aluminium or titanium used here (α=20×10$^{-6}$ K$^{-1}$ and α=8.5×10$^{-6}$ K$^{-1}$, respectively).

Conducting a conventional uniform anti-adhesion treatment across the carrier wafer was observed to result in a non-isotropic and non-uniform wrinkling surface morphology across the substrate (i.e. wrinkled and non-wrinkled areas of the substrate, with a variable wavelength of undulations), whilst significant deviations from the presently described process or the substrate composition, such as exclusion of the n-methyl-2-pyrrolidone treatment and/or one of the layers of the multi-layered substrate structure, were observed to nullify the wrinkling morphology and result instead in either a smooth or cracked surface morphology of the PDMS substrate.

From the teaching provided by the present disclosure, a person skilled in the art will understand that the combination of:

(i) the selective anti-adhesion treatment process applied to a carrier substrate, whereby an outer peripheral region of the substrate provides a strong adhesion region and the area of the substrate within the outer peripheral region provides an anti-adhesion central region, (ii) the elasticity gradient provided by the successive thin-film layers of PDMS (L1 and L2) having decreasing ratios of crosslinking agent to base material, (iii) placing the carrier substrate in an organic solvent for a period of time to induce swelling in those PDMS layers, constrained by the strong peripheral adhesion to the carrier substrate and an overlying Parylene layer (L3), (iv) applying a further PDMS layer (L4) to provide a "stiff-soft" interface with the preceding Parylene layer (L3), and (v) diffusion of the solvent during vacuum deposition of a subsequently applied thin-film layer of Parylene (L5), gives rise to the permanent micro-scale wrinkled surface morphology generated in the subsequently applied thin-film layer of parylene (L5). This in turn enables the formation of the layer of electrically conductive material on the micro-scale wrinkled surface of the parylene such that the electrically conductive material has a micro-scale wrinkled surface morphology conforming to that of the wrinkled Parylene layer (L5). The process thus provides the basis for a bottom-up, wafer-scale fabrication process for producing flexible structures that include a plurality of thin-film layers of elastomeric material and at least one layer of micro-wrinkled electrically conductive material, which in turn enables the use of photolithographic techniques for, firstly, patterning and accurately aligning multiple micro-wrinkled conductive layers and, secondly, producing tunable microstructure layers. As shall be described further below, the process features (i)-(v) described above can support the creation of multiple wrinkled Parylene layers within a device structure. Given this teaching, the skilled person will be able, by routine experimentation, to find variations of the particular embodiments and examples provided herein, in terms of process parameters, layer thicknesses and elasticities, etc., that provide useful results for particular practical applications of the present invention.

Figure 12:
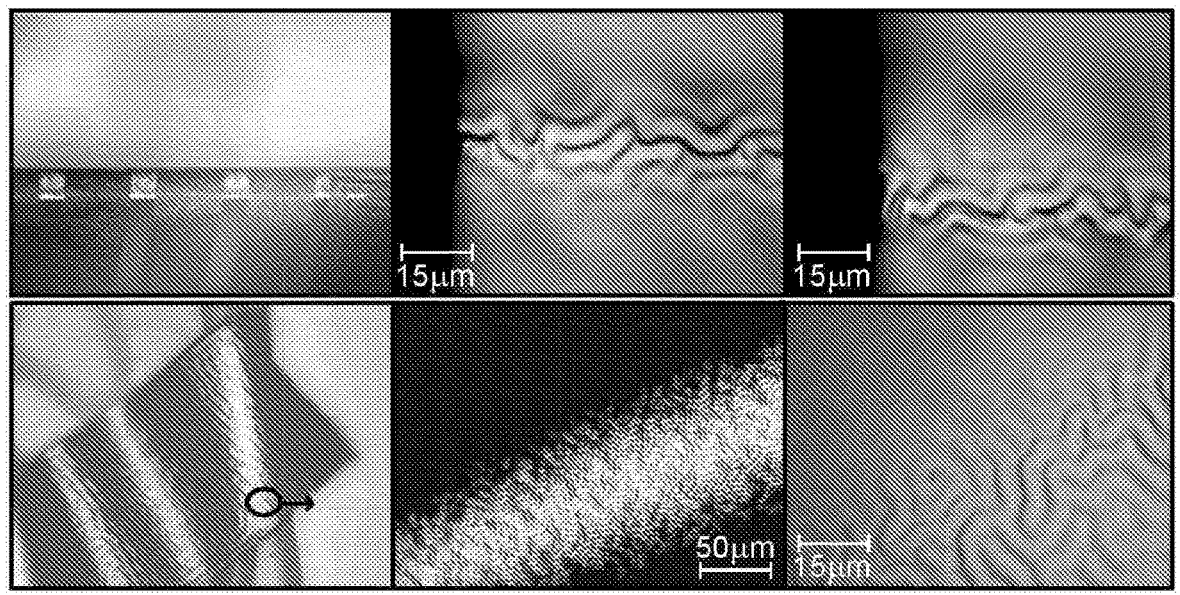
FIG. 12 illustrates the wrinkled tracks' resilience to 180° bending.

The functionalised surface morphology provides mechanical relief over large compressive and strain stresses due to the increased effective surface that the wrinkling provides. This allows the film to be bent up to 180° without failure, as exemplified in FIG. 12. Any induced crack formation, such as exemplified in FIG. 13 where the film was intentionally damaged with a sharp blade, is obstructed and retained only within a few micrometres near the site of damage since the distribution of the undulations effectively blocks any propagation of metal discontinuities, constricted on one plane until a perpendicular wave front is reached. This behaviour is to be contrasted with the planar and smooth conventional metallisation processes on PDMS (typically limited on the nanometre scale) where cracks, originating from localised stress points, propagate across the film.

Successful development of PDMS-based flexible and wireless LC sensors requires achieving high quality (i.e. low resistivity) thick ($t \geq 1$ μm) metal tracks for the sensor inductive structures in order to provide a sufficiently high-quality factor for the sensors (i.e. the quality factor has a 1/R dependency) that can enable a wireless readout via means of inductive coupling, with tracks that are able to demonstrate resilience to failure (ie. cracking) during deposition, detachment from the carrier wafer, bending and compressive deformation.

Figure 8:
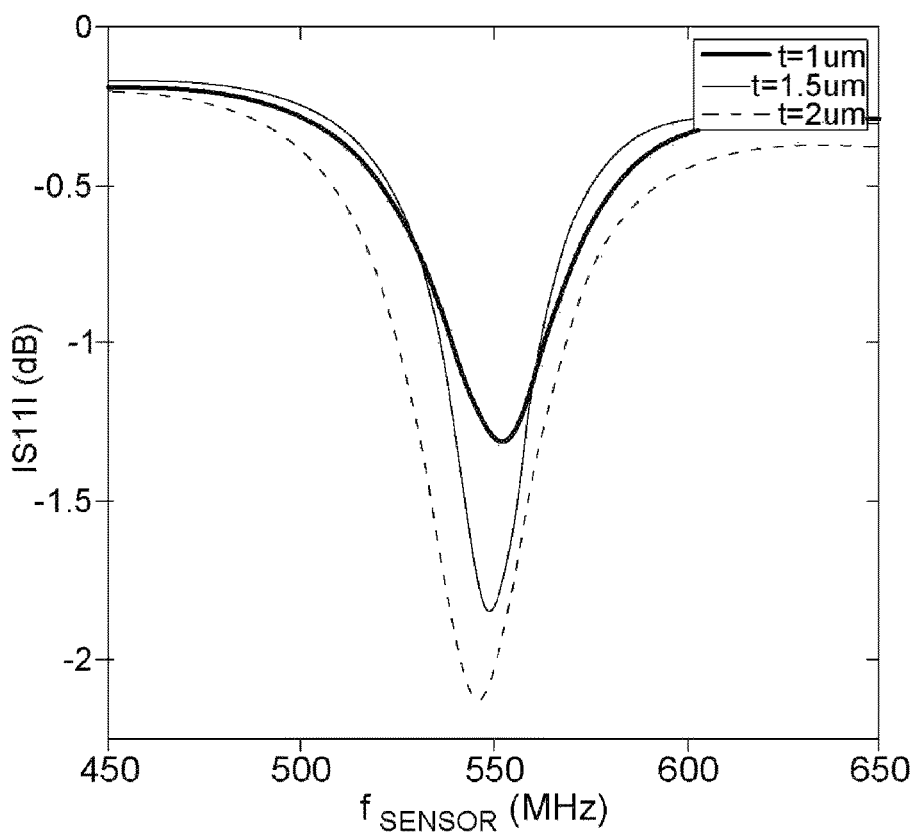
FIG. 8 is a graph showing sensor $S_{11}$ magnitude versus thickness for the three thicknesses of metallisation shown in FIG. 8.
Figure 9:
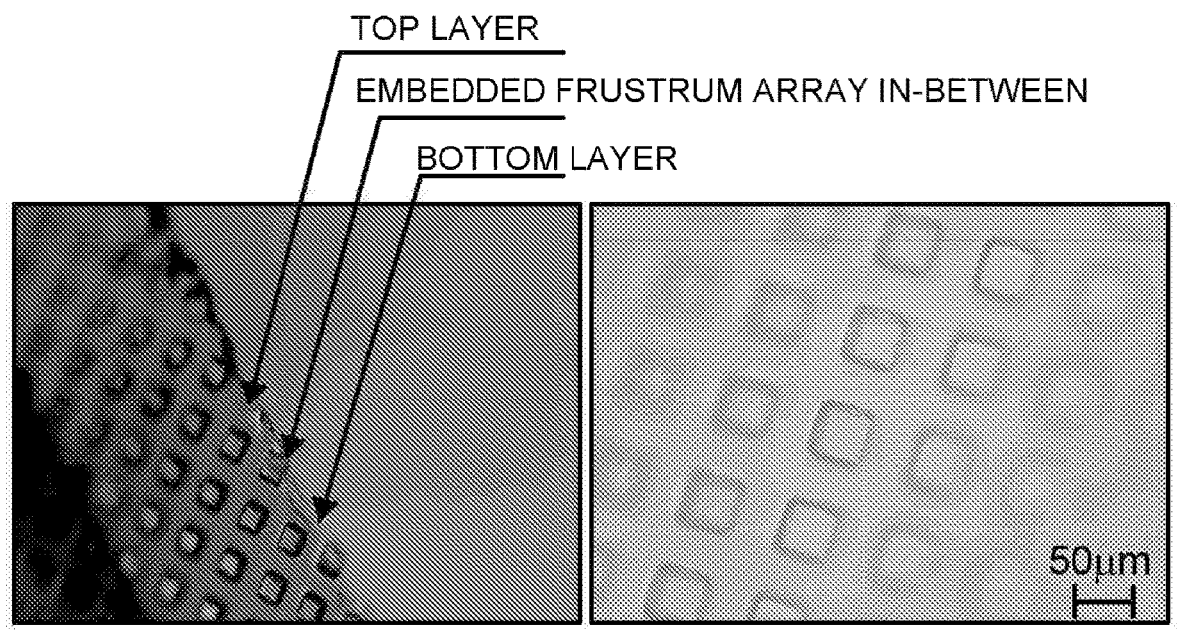
FIG. 9 illustrates the embedded thin-film microstructured layer of the sensor.

Increased metal thickness results in an increased return loss amplitude $|S_{11}|$ (i.e. increased wireless readout distance), as shown in FIG. 8, due to the higher quality factor that a thicker metallisation provides. In addition, the resistivity of the wrinkled aluminium metallisation was found to be uniform across the film with a very low value of $\bar{\rho}=(10.7\pm1.6)\ 10^{-8}$ Ω.m, effectively identical to that obtained when aluminium was deposited directly onto the silicon wafer (ie. SiO$_2$/Si), with a value in this case of $\bar{\rho}=(10.4\pm2.1)\ 10^{-8}$ Ω.m.

FIG. 5C illustrates the interlayer microstructuring process which, in contrast to the prior art, enables direct bottom-up formation of embedded thin-film microstructured layers on thin-film PDMS substrates without the need of detaching the substrate, e.g. from a silicon etched mould, movement, repositioning and lamination to a substrate as in the prior art.

As shown, a thin-film 1:10 PDMS layer (L8) microstructured with an equiaxial frusta array is formed directly atop the first inductor layer (L6/L7) successively by:

5C-(i) Formation of a crack-free sacrificial photoresist mould film with the negative image of the microstructure selectively on the central area of the carrier substrate (i.e. inside the outer peripheral region 320).

To counter the thermal expansion that PDMS suffers due to its elastomeric nature, and which may result in severe crack formation of the sacrificial photoresist layer due to thermal mismatch (which impedes the preferential dissolution and expulsion of the sacrificial mould), the thermal activation of the photoresist layer, as well as the crosslinking of the encapsulating PDMS layer in the next step, may be optimized by ramping down the temperature of the wafer to ambient conditions over 105 min following each thermal crosslinking and retaining the wafer at an angled position during the cool-down (FIG. 15a), successfully yielding a crack-free sacrificial photoresist micro-mould.

5C-(ii) Encapsulation of the sacrificial layer with a thin-film spin-coated PDMS layer (L8/L9), optimised thermal PDMS crosslinking and formation of two exposed reservoir regions and two strongly bound unstructured regions across the outer periphery of the wafer (as a consequence of the selective anti-adhesion process described previously).

5C-(iii) Preferential dissolution with, for example, n-methyl-2-pyrrolidone (or any other similar biocompatible organic solvent that allows photoresist dissolution with low intensity swelling of the PDMS) of the sacrificial photoresist layer across the two reservoir regions via capillary forces with the wafer in a perpendicular position and formation of the embedded microstructured layer. The solvent used can (as in this case) be the same solvent as used in step 5B-(ii). The sacrificial photoresist dissolves very rapidly in the organic solvent (~1-2 min). However, when a further wrinkled parylene layer is to be formed subsequently (e.g. layer L11 in this example), the wafer may be immersed in the solvent for an extended period of time, e.g. 12 hours, to perform the same function as step 5B-(ii) in relation to the wrinkling of layer L5. This is discussed further below.

5C-(iv) Thermal drying and desiccation.

Figure 14:
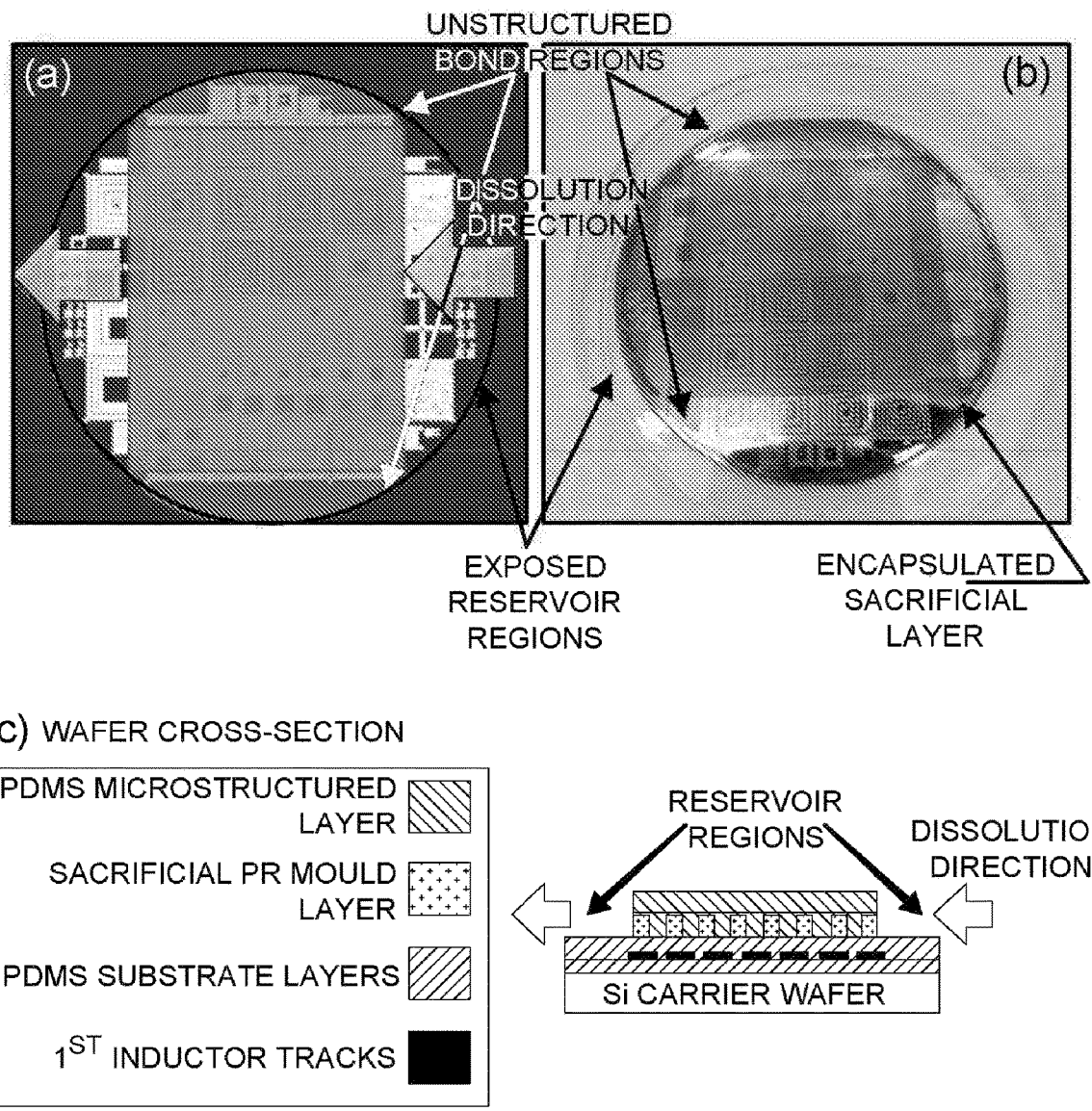
FIG. 14 illustrates reservoir formation and preferential dissolution in the microstructure microfabrication process illustrated in FIGS. 3C and 5C: (a) Preferential direction of dissolution of sacrificial photoresist layer; (b) photograph of the embedded sacrificial mould on the surface of the first inductor layer prior to dissolution; (c) cross-section of the sensor structure overlooking the reservoir areas (the unstructured bond regions lie at the transverse direction of the cross-section and are not shown).

Formation of the embedded microstructured layer is achieved by encapsulating the sacrificial photoresist (PR) containing the microstructured cavities via a thin-film spin-coated PDMS layer (L8/L9). This is achieved, as depicted in FIG. 14, by selectively forming photolithographically (i.e. step 5C-(i) above) the PR sacrificial layer centrally on the substrate (encapsulated sacrificial layer, FIG. 14) and concurrently, during the subsequent step (ie. step 5C-(ii), PDMS encapsulation), by retaining exposed (i.e. non-encapsulated) the two side areas of the substrate (exposed reservoir regions, FIG. 14) in order to serve as reservoir regions (step 5C-(ii), exposed reservoir regions). The latter is facilitated through the use of a polyimide (PI) adhesion film on these areas serving as temporary shield during spin-coating of the encapsulation layer. In contrast the top and bottom areas of the substrate (step 5C-(ii), strongly bound unstructured regions) are retained non-shielded and hence non-structured, in order to allow a strong uniform bond of the PDMS substrate (L7) with the encapsulating PDMS layer (L8) (FIG. 14, unstructured bond regions). The surface of the PDMS substrate L7 is furthermore treated at that stage with $O_2$ plasma for 30 seconds to enable a strong bond of the encapsulation PDMS layer (L8) with the underlying PDMS substrate (L7). The temperature of the $O_2$ plasma chamber is kept below 53° C. during this processing stage as a higher temperature was found to result in crack formation of the sacrificial photoresist mould. The PDMS encapsulation layer (L8/L9) is spin-coated thereafter and optimally thermally crosslinked at 22 min/90° C. (instead of the recommended 35 min/100° C. for Sylgard 184 which was found to lead to undesired cracking of the sacrificial phototoresist mould) and by the process described above, effectively coating everything besides the two shielded reservoir regions (step 5C-(ii), optimised crosslinking).

Because this PDMS layer L8 is directly deposited at the surface of the procured, now hydrophilic, PDMS film substrate L7 (due to the $O_2$ plasma), it allows a very strong bond between the two layers, since, at the interface, the uncured liquid diffuses in the PDMS substrate L7 during the thermal crosslinking of the deposited elastomer.

Figure 15:
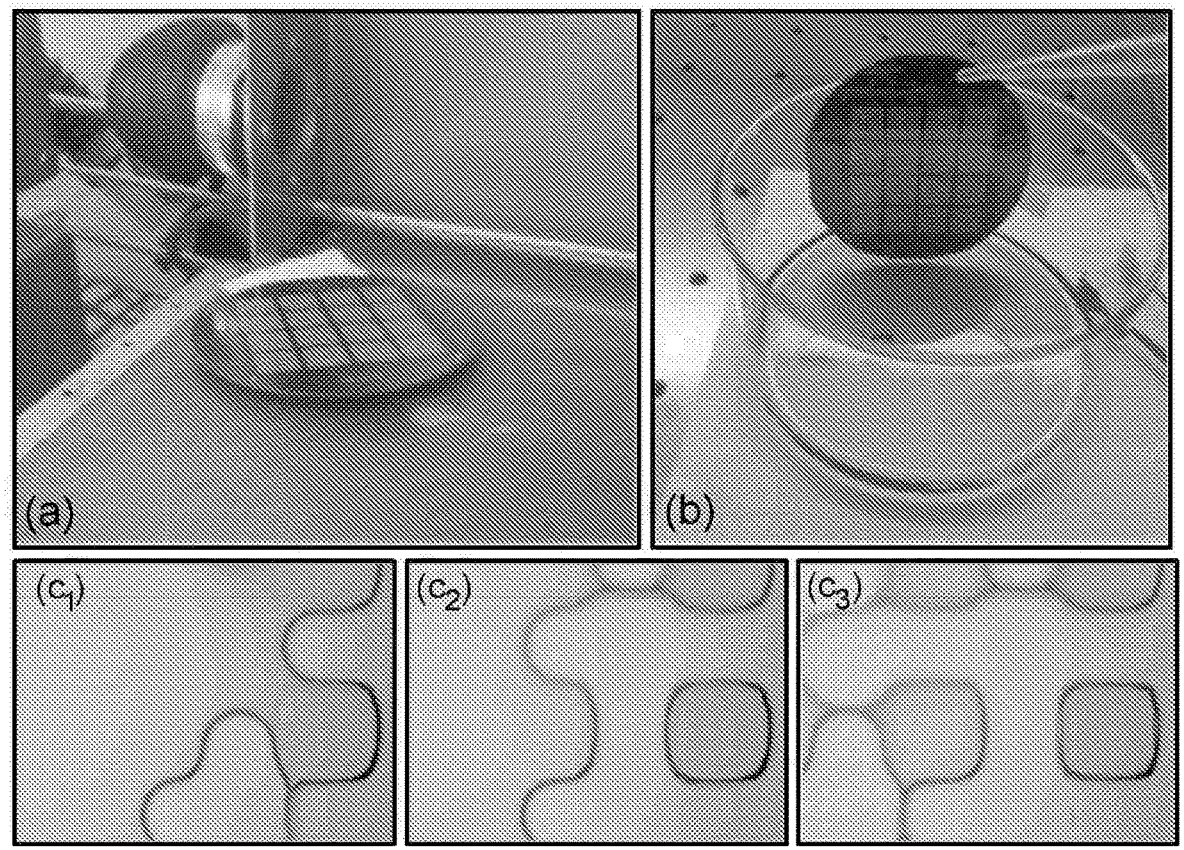
FIG. 15 illustrates the (a) an optimized thermal ramp-down step following encapsulation of the sacrificial mould (b) a preferential dissolution technique of a wafer containing arrays of identical 10×10 mm² sensors and (c) microcapillary forces in action during formation of the microstructured layer.

Dissolution of the sacrificial photoresisist mould is achieved by first removing the temporary PI shields at the reservoir regions and by placing the wafer in a n-methyl-2-pyrrolidone bath for 12 hours (see above re 5C-(iii)), followed by a preferential expulsion through the exposed two reservoir regions across one direction, as shown in FIG. 14, via capillary forces as shown in FIG. 15c. The latter is achieved by placing the wafer at an angled perpendicular position to the dissolver bath, while a pipette is utilised to reduce the time required for the expulsion process from about 3 hours to about 5 minutes, by depositing intermittently small quantities of the dissolver on the top reservoir region as shown in FIG. 15b. Having the wafer at a perpendicular position and depositing iteratively small quantities of the dissolver via use of a pipette on one of the reservoir regions laying now on the top, as shown in FIG. 15b, expedites (as low as 5 minutes) the expulsion of the dissolved sacrificial micromould photoresist layer that is driven by capillary forces to the second reservoir region laying now at the bottom (see FIG. 14a: dissolution direction). Under the influence of the capillary forces, the liquid flows uninterrupted throughout the microchannels preferentially across one direction (see FIG. 15, $c_1 \rightarrow c_3$) as the microstructured layer acts as an isotropic and symmetric microfluidic structure of a hydrophobic nature due to PDMS. In contrast simply placing the wafer at this position to drain, the dissolved sacrificial layer is similarly expelled over time to the bottom reservoir regions but much more slowly (>3 hours) and with lower yield across batches (due to occasional entrapment of small quantities of the dissolved sacrificial layer within the structure).

This is then followed by a thorough Deionization (DI) water bath, and a thermal and vacuum dry-out in a desiccator to ensure that any trapped liquid residues are expelled (step 5C-(iv)). The reservoir regions thus allow direct access to the embedded sacrificial layer, thereby enabling the formation of the thin-film embedded microstructured layer, bottom-up directly on the substrate, in contrast to current soft-lithography processes, whilst planarity of the film during this processing stage is ensured by the non-structured outer bounds of the substrate that firmly keep it in place, due to the strong bond of the encapsulating layer with the unstructured peripherical areas of the substrate.

Figure 16:
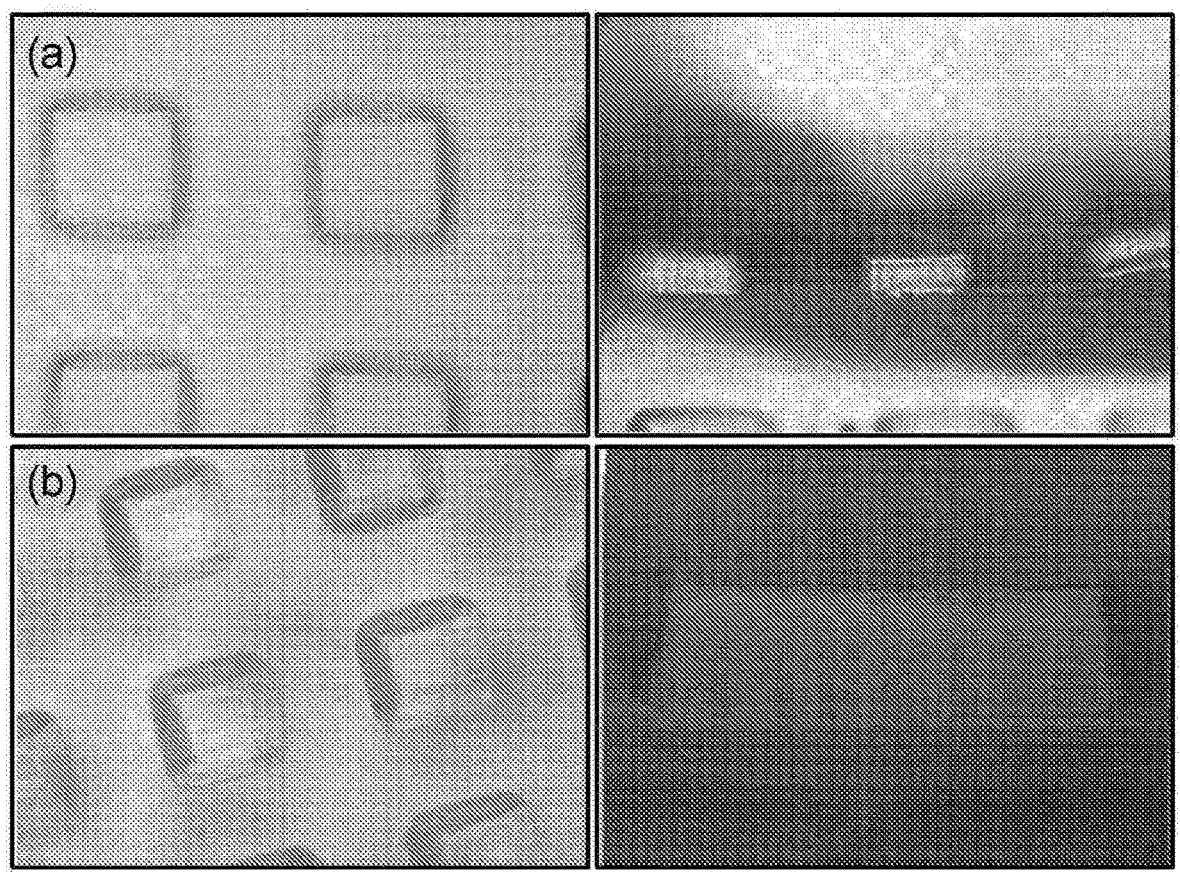
FIG. 16 illustrates the tunable capacity of the frustum side-wall angle to 90° and 74° of the microstructure layer of the sensor enabled by controlling the UV exposure during formation of the sacrificial photoresist layer.

In contrast to conventional soft-lithography microstructuring, based on potassium hydroxide (KOH) etching of Si moulds followed by encapsulation with PDMS, that results in a frustum with a fixed 54.7° side-wall angle, direct photopatterning of the sacrificial layer enables a tunable side-wall angle of the frustum, depending on the UV exposure as shown in FIG. 16, which can provide additional design freedom on the compressive deformation that a frustum experiences and hence an improved tuning capacity of the mechanical sensitivity to compression of the sensors. A side-wall angle of ~74° was selected here for the developed sensors since it results in a reduction of approximately 3 orders of magnitude of the effective Young's modulus of the frustum, and hence to an improved sensitivity to deformation.

As shown in FIGS. 3D and 3E, a second aligned inductor layer wrinkled metallisation process, dry-out, encapsulation and peel-off process includes the following steps.

Figure 10:
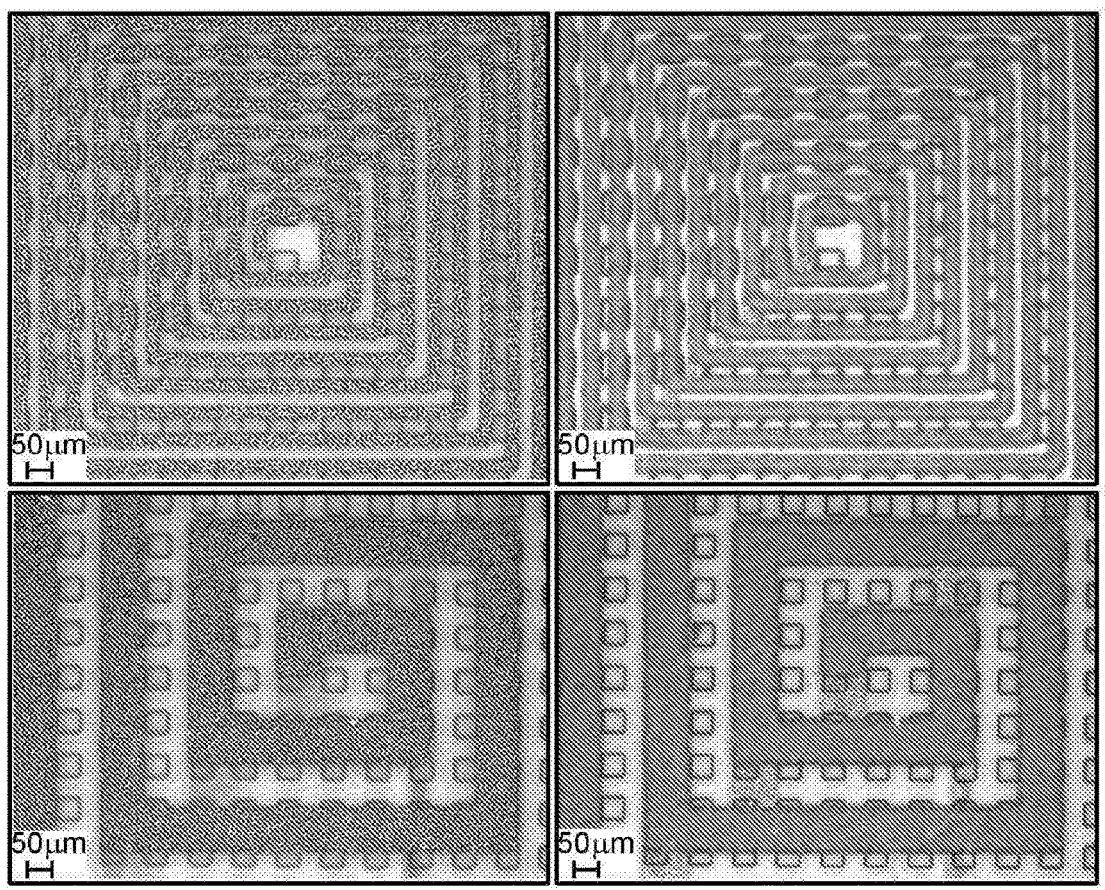
FIG. 10 illustrates the high alignment yield of multi-coiled double inductive structures with a track width as low as 25 µm, with (left) the top inductor and (right) the bottom inductor.

3D-(i) The aligned second inductor layer and wrinkled surface morphology is formed by iterating steps (iii)-a, 5B-(iii)-b and 5B-(iv) of the micro-wrinkling process (FIGS. 3B and 5B as described above), to create layers L10 to L12, including wrinkled Parylene layer L11 and second wrinkled metallic layer L12, with the provisions of (a) utilising micro-alignment photolithography design features included in the photomask for the first inductor layer, and hence in the pattern of the first inductor layer itself, and in the photomask for the second inductor layer, to enable exact and accurate alignment of the first and second inductor structures of the sensor arrays across the wafer and, preferably, (b) forming a small via at the rim of the encapsulated reservoir regions of the microstructured layer (L8/L9) prior the metal deposition. Examples of highly aligned multi-coiled inductors with track widths of as low as 25 µm achieved via the present process are shown in FIG. 10.

3E-(ii) Thermal dry-out and desiccation.

3E-(iii) Encapsulation of the second inductor layer with a thin-film PDMS layer L13 via spin-coating and thermal crosslinking; and 3E-(iv) Cut-out with blade film across the active anti-adhesion region of the carrier wafer and manual peel-off the film with the sensor arrays.

Referring to 3D-(i) above, the wrinkling mechanism for layers L11/L12 can be further explained as follows.

The wrinkled second inductor metallization (L12) leverages the same mechanism of the low intensity swelling of layers L1 and L2, since the generation of the mechanical compressive instability effectively originates from there, when immersed for the (same) set time in the organic solvent (in step 5C-(iii)) and during L11 Parylene vacuum deposition. Layers L1, L2, L3 and L4, together with the strong peripheral adhesion, play the same role in the wrinkling of layer L11 as they do in the wrinkling of layer L5.

In this case, as previously, immersion in the organic solvent in step 5C-(iii) leads again to a low intensity swelling of the constricted L1-L2 PDMS layers between the L3 Parylene layer and the rigid carrier wafer, which similarly undergo an abrupt volume change as the swollen state is relaxed again under vacuum due to solvent diffusion, when the L11 Parylene layer is deposited. An osmotic pressure across the bulk of the film is similarly generated, due to the latter and the complex gradient mechanical properties (elasticity) of the film structure, lead to the emergence of in-plane equibiaxial compressive strains here at the upmost (L10) PDMS layer interface that in turn lead to buckling of the film and hence a labyrinthine wrinkling pattern of the surface, whilst the Parylene deposition (L11) concurrently aids in the stabilisation (frosting) of the wrinkle formation that is retained irrespectively of the L12 metal microscale thickness deposition, as previously.

If the L10 (1:5 PDMS) is omitted from the film structure and the L11 Parylene layer is instead directly deposited onto the surface of L9 (1:10 PDMS), this leads instead to the dissipation of the surface wrinkling morphology (i.e. a planar surface results instead) and the generation of severe crack formations during metalisation despite the introduction of the Parylene coating L11. This is because the unconstrained (ie. due to the exposed reservoir regions) microstructured layer effectively absorbs the elastic shear (in-plane) buckling deformation at the interface during the Parylene deposition (L11) and experiences also intensified compression over the normal axis at the free-standing areas during the metal deposition (L12). The introduction of the L10 (1:5 PDMS) prior the deposition of the Parylene L11 layer restores the complex mechanical properties and structural stability of the film, since it is mirroring the elasticity gradient of layers L1 and L2 and also bounds the underlaying microstructured layer, and hence enables the generation of the same frosted labyrinthine wrinkling morphology (ie. $\lambda \sim 7.5$ µm for the process parameters described herein) across the surface film interface of L10-L11 prior the deposition of the second inductor microscale metalisation (L12) of the film as previously.

This approach is also expected to further provide for the generation of the same wrinkled morphology for a subsequent third metallic inductor(s) layer, if it was desired (and potentially for further inductor layers if the described method is similarly adapted appropriately).

It may be noted that a softer 1:10 PDMS (1.7M Pa) composition for the microstructured layer (L8 and L9) enables an optimal performance of the pressure sensor to compressive loads, since the lower Young's modulus increases the deformation that the microstructured layer L8/L9 experiences which in turn significantly improves the sensitivity of the sensor device. The encapsulation of the first inductor structure L6 with 1:10 PDMS layer L7 is selected to provide the maximal adhesion with the L8 microstructured features and strong resilience (structural stability) to detachment to shear forces when the sensor experiences dynamical force (tactile) loads (i.e. no detachment of the features and hence of the structure).

With further reference to the micro-scale wrinkling processes and mechanisms discussed herein, the present inventors' understanding is that the complex variability (gradient) of the mechanical elasticity (stiffness) of adjacent layers of the films generate "soft-stiff" interfaces amongst them, e.g. L9/L10, which in turn enable the propagation of the mechanical compressive instability across film, generated at L1/L2 as previously described in detail, and selectively towards the upper interfaces, L4/L5 and L10/L11 in the present examples, to be permanently wrinkled prior to metallisation.

In general, [see again: J. Rodriguez-Hernandez, "Wrinkled interfaces: Taking advantage of surface instabilities to pattern polymer surfaces", Progress in Polymer Science, 2015, 1-41], a bound (e.g. constricted to a rigid wafer) elastomer system comprised of two constituents with a gradient elastic modulus, e.g. a softer elastomer substrate, serving as the "foundation", and a more rigid layer deposited on top, behaving as a solid "skin" at their interface, forms a simple bi-layer elastomer system. Upon mechanical stress overcoming a critical loading value (e.g. introduced via stretching or heating, application of a compressive stress, upon cooling, or by solvent evaporation and osmotic pressure if the bulk material is swollen) and the subsequent removal of the stress applied, allows the film "foundation" to relax thus leading to a wavy structure known as "wrinkling". A difference in the stiffness at the polymer interface, i.e. between the "skin" and the "foundation", is required in order to drive the interface surface bending out of plane, under the influence of the mechanical stimuli, and promote the wrinkle formation. The "skin" and "foundation" layers vary their dimensions differently, due to their different mechanical properties (Young's modulus and Poisson ratio), and as a consequence a compressive force is generated on the interface leading to buckling.

The LC sensor layer structure described herein can be viewed effectively as a collection of such "soft-stiff" and "stiff-soft" interfaces generated by the adjacent layers of the film, i.e. L1/L2, L2/L3, L3/L4, L4/L5, L5/L7, (L7-L9)*/L10 and L10/L11 (*L7-L9 are all 1:10 PDMS here, hence L7-L9 can be considered as one effective layer). These interfaces successively promote the compressive mechanical buckling instability, stemming from the shrinkage of the swelled L1 and L2 layers bound to the carrier wafer, across the film and towards the upmost interface during either the L5 or L11 Paralyne layer vacuum deposition respectively. With regard to the L8/L9 microstructured layer, the L10 layer is furthermore required, as previously described, to constrain the L8/L9 layers as otherwise the wrinkling dissipates. If the microstructured 1:10 PDMS layer (L7-L9) is instead completely omitted and L10 (1:5 PDMS)/L11 (Parylene) layers are only deposited in their stead, which effectively is an exact repetition of the layers L4/L5, the wrinkling was found to emerge again as expected, as long as, the wafer is placed in the organic solvent bath prior to introduce the required low-intensity swelling.

Spatial and angular self-alignment of the two inductor layers of the sensors is achieved by leveraging the optical transparency of PDMS and Parylene (ie. of the sensor structure) and via the use of typical photolithographic micro-alignment design features at, typically, two sites (e.g. 4 micro-crosses) across the substrate, which are deposited concurrently with the first inductor layer (i.e. as part of the pattern of layer L6), and used respectively when the typical UV mask aligner equipment positions the photomask of the second inductor layer L12, which has identical features, during photolithographic formation of the corresponding lift-off photoresist of the second inductor layer prior to metallisation. This is accomplished by optically aligning during processing (in industrial settings this is automated) the micro-alignment features of the first inductor layer L6 with the features of the photomask of the second inductor layer L12 concurrently at both sites to ensure wafer-scale alignment (ie. for correct angular and spatial alignment across the wafer).

Figure 17:
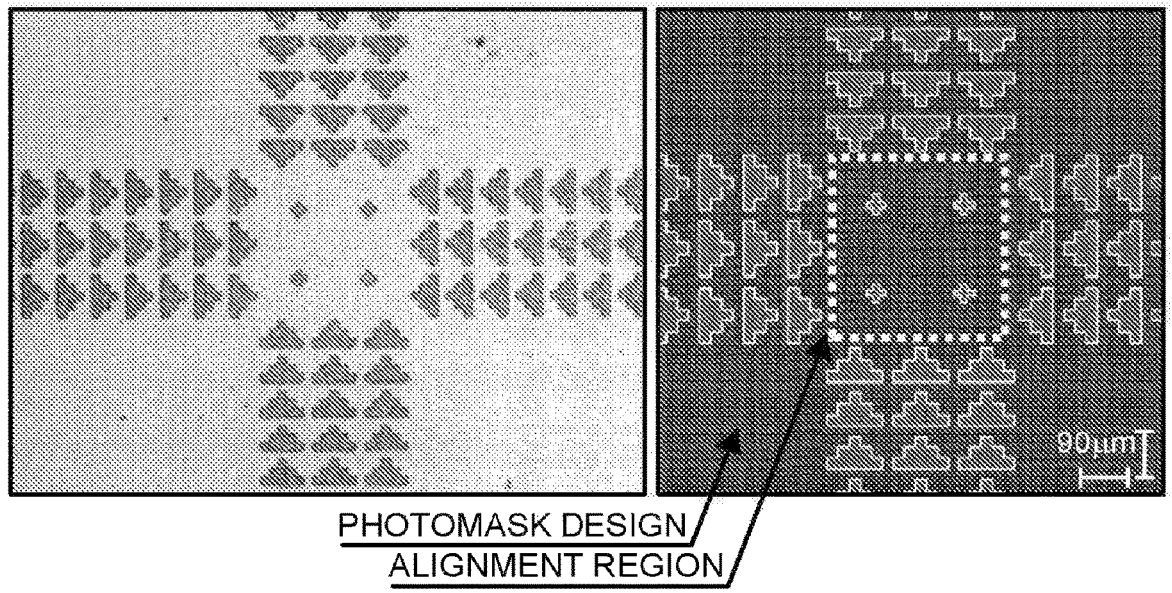
FIG. 17 illustrates the photolithographic micro-alignment structures.

The micro-alignment features are depicted in FIG. 17 and a typical photolithographic bottom-up alignment process allows a very low misalignment error in the order of <3 µm (dependant on the UV mask aligner equipment and photomask).

The latter further relates to the superiority of the present bottom-up process, over the typical current state-of-the-art, which involves separate layer development and mechanical alignment, and hence the high yield of the sensor arrays on a wafer-scale that may be provided by the present invention.

Figure 18:
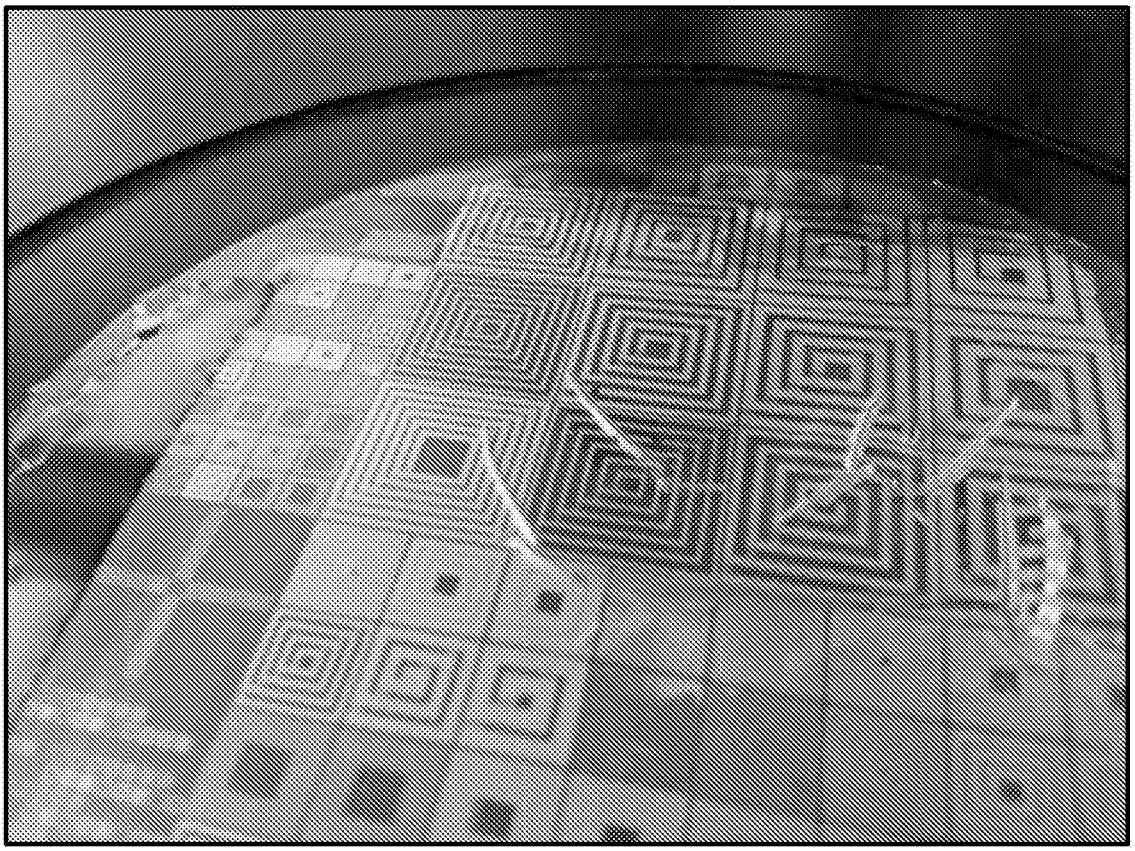
FIG. 18 illustrates the inflation defect of the sensor array film when no via is created and the reservoirs are held encapsulated during deposition of the aligned second inductor layer.

Without the presence of the via referred to above, the embedded microstructured layer may partly inflate, as shown in FIG. 18, during metal deposition of the second inductor layer due to the high vacuum of the sputterer. The via enables trapped air within the embedded micro-structured layer to escape and is achieved by simply cutting out a very small section of the film (eg. <1×1 mm²) with a blade prior the second inductor layer metallisation at the rim (interface) of the encapsulated micro-structured area and the now encapsulated reservoir region.

The two floating inductors of the LC sensor structure form an inductively and capacitively highly coupled LC system as they are aligned and very close together (i.e. thin-film thickness between them leads to a very high coupling coefficient $k_{sensor}$~1).

As described herein, the present invention enables wafer-scale production of highly flexible thin film devices incorporating highly flexible electrically conductive layers, with very accurate alignment of multiple electrically conductive patterns on different layers, exemplified by the inductive structures of the LC wireless sensor described herein, and further enables the production of sensor microstructures having parameters that can be tuned and varied across an array of devices.

Improvements and modifications may be incorporated without departing from the scope of the invention as defined by the claims appended hereto.

The invention claimed is:

1. A method of producing a flexible structure that comprises a plurality of thin-film layers of elastomeric material and at least one layer of micro-wrinkled electrically conductive material, the method comprising:
   a) applying a selective anti-adhesion treatment process to a carrier substrate whereby an outer peripheral region of the substrate provides a strong adhesion region and the area of the substrate within the outer peripheral region provides an anti-adhesion central region;
   b) forming, on the carrier substrate, a first plurality of successive thin-film layers of PDMS, each of the successive thin-film layers of PDMS having a smaller ratio of crosslinking agent to base material and hence a higher Young's modulus than a preceding one of the thin-film layer of PDMS;
   c) forming, on the last-formed thin-film layer of PDMS, a first thin-film layer of Parylene;
   d) placing the carrier substrate in an organic solvent for a first period of time to induce swelling in the first plurality of thin-film layers of PDMS;
   e) forming, on the first thin-film layer of Parylene a first further thin-film layer of PDMS;
   f) forming by vacuum deposition, on the first further thin-film layer of PDMS, a second thin-film layer of Parylene in which a permanent micro-scale wrinkled surface morphology is generated as a consequence of diffusion of the organic solvent from the first plurality of thin-film layers of PDMS during said vacuum deposition, thus providing a first micro-scale wrinkled Parylene layer;
   g) forming and patterning a first layer of electrically conductive material on the first micro-scale wrinkled Parylene layer such that the first patterned electrically conductive material has a micro-scale wrinkled surface morphology conforming to that of the first micro-scale wrinkled Parylene layer, thus providing a first micro-scale wrinkled electrically conductive pattern layer.

2. The method of claim 1, wherein the selective anti-adhesion treatment process applied to the carrier substrate comprises a process whereby the outer peripheral region of the substrate is made highly hydrophilic and the central area of the substrate within the outer peripheral region is made highly hydrophobic.

3. The method of claim 1, wherein the organic solvent and the first period of time are selected to induce a degree of swelling in the first plurality of thin-film layers of PDMS that causes the permanent micro-scale wrinkled surface morphology to be generated in the first further thin-film layer of PDMS.

4. The method of claim 1, wherein the organic solvent is n-methyl-2-pyrrolidone, dioxane, dimethyl carbonate, pyridine or dimethylformamide.

5. The method of claim 1, wherein the first further thin-film layer of PDMS has a Young's modulus equal to that of the last-formed layer of the first plurality of thin-film layers of PDMS.

6. The method of claim 1, wherein the carrier substrate is a silicon wafer.

7. The method of claim 1, wherein a second micro-scale wrinkled electrically conductive pattern layer is formed by:
   placing the carrier substrate in an organic solvent for a second period of time to re-induce swelling in the first plurality of thin-film layers of PDMS;
   forming one or more additional thin-film layers of PDMS on the uppermost layer of the preceding structure;
   forming by vacuum deposition, on the uppermost of the additional thin-film layers of PDMS, a third thin-film layer of Parylene in which a permanent micro-scale wrinkled surface morphology is generated as a consequence of diffusion of the organic solvent from the first plurality of thin-film layers of PDMS during said vacuum deposition, thus providing a second micro-scale wrinkled Parylene layer; and
   forming and patterning a second layer of electrically conductive material on the second micro-scale wrinkled Parylene layer such that the second patterned electrically conductive material has a micro-scale wrinkled surface morphology conforming to that of the first micro-scale wrinkled Parylene layer, thus providing a second micro-scale wrinkled electrically conductive pattern layer.

8. The method of claim 1, further comprising forming one or more additional layers of PDMS on the first micro-scale wrinkled electrically conductive pattern layer and patterning one or more of the one or more additional thin-film layers of PDMS to create a 3D microstructure.

9. The method of claim 8, wherein the 3D microstructure is formed photolithographically.

10. The method of claim 8, wherein the 3D microstructure comprises an array of individual frustum arrays and each of the first and second micro-scale wrinkled electrically conductive pattern layers comprises an array of individual inductive structures, and wherein each inductive structure of each micro-scale wrinkled electrically conductive pattern layer is aligned with a corresponding frustum array of the 3D microstructure and a corresponding inductive structure of the other micro-scale wrinkled electrically conductive pattern layer to provide an array of individual devices usable as wireless LC sensors.

11. The method of claim 1, wherein each layer of electrically conductive material is patterned using photolithography.

12. The method of claim 1, wherein the patterning of each layer of electrically conductive material provides an array of individual electrically conductive structures corresponding to an array of individual devices.

13. The method of claim 12, wherein one or more of the individual electrically conductive structures has one or more physical parameters that is different from one or more of the other individual electrically conductive structures.

14. The method of claim 1, wherein each layer of electrically conductive material is a metallic layer.

15. A flexible structure that comprises a plurality of thin-film layers of elastomeric material and at least one layer of micro-wrinkled electrically conductive material, the structure comprising:
  a first plurality of successive thin-film layers of PDMS, each of the successive thin-film layers of PDMS having a smaller ratio of crosslinking agent to base material and hence a higher Young's modulus than a preceding one of the thin-film layer of PDMS;
  a first thin-film layer of Parylene;
  on the first thin-film layer of Parylene, a first further thin-film layer of PDMS;
  on the first further thin-film layer of PDMS, a second thin-film layer of Parylene having a permanent micro-scale wrinkled surface morphology, providing a first micro-scale wrinkled Parylene layer;
  a first layer of electrically conductive material on the first micro-scale wrinkled Parylene layer having a micro-scale wrinkled surface morphology conforming to that of the first micro-scale wrinkled Parylene layer, providing a first micro-scale wrinkled electrically conductive pattern layer.

16. The structure of claim 15, wherein the first further thin-film layer of PDMS has a Young's modulus equal to that of the last-formed layer of the first plurality of thin-film layers of PDMS.

17. The structure of claim 15, further comprising:
  one or more additional thin-film layers of PDMS on the uppermost layer of the preceding structure;
  a third thin-film layer of Parylene having a permanent micro-scale wrinkled surface morphology, providing a second micro-scale wrinkled Parylene layer; and
  a second layer of electrically conductive material on the second micro-scale wrinkled Parylene layer such that the second patterned electrically conductive material has a micro-scale wrinkled surface morphology conforming to that of the first micro-scale wrinkled Parylene layer, thus providing a second micro-scale wrinkled electrically conductive pattern layer.

18. The structure of claim 15, further comprising one or more additional layers of PDMS on the first micro-scale wrinkled electrically conductive pattern layer, one or more of the additional layers of PDMS patterned to provide a 3D microstructure.

19. The structure of claim 15, wherein each layer of electrically conductive material is patterned using photolithography.

20. The structure of claim 15, wherein each layer of electrically conductive material is a metallic layer.

* * * * *